United States Patent
Sheng et al.

(10) Patent No.: US 10,995,083 B2
(45) Date of Patent: May 4, 2021

(54) COCRYSTAL OF 2-(6-METHYL-PYRIDINE-2-YL)-3-YL-[6-AMIDE-QUINOLINE-4-YL]-5,6-DIHYDRO-4H-PYRROLE[1,2-B]PYRAZOLE, PREPARATION METHOD THEREFOR, AND PHARMACEUTICAL COMPOSITION

(71) Applicant: Hangzhou SoliPharma Co., Ltd., Zhejiang (CN)

(72) Inventors: Xiaohong Sheng, Zhejiang (CN); Xiaoxia Sheng, Zhejiang (CN); Jing Wang, Zhejiang (CN)

(73) Assignee: Hangzhou Solipharma Co., Ltd., Hangzhou (CN)

( * ) Notice: Subject to any disclaimer, the term of this patent is extended or adjusted under 35 U.S.C. 154(b) by 0 days.

(21) Appl. No.: 16/496,023

(22) PCT Filed: Mar. 21, 2017

(86) PCT No.: PCT/CN2017/077459
§ 371 (c)(1),
(2) Date: Sep. 20, 2019

(87) PCT Pub. No.: WO2018/170724
PCT Pub. Date: Sep. 27, 2018

(65) Prior Publication Data
US 2020/0017470 A1    Jan. 16, 2020

(51) Int. Cl.
*C07D 401/14*    (2006.01)
(52) U.S. Cl.
CPC ........ *C07D 401/14* (2013.01); *C07B 2200/13* (2013.01)

(58) Field of Classification Search
CPC ........ C07D 401/14; A61P 35/00; A61P 11/00; C07B 2200/13
USPC ........................................................ 546/167
See application file for complete search history.

(56) References Cited

U.S. PATENT DOCUMENTS

| | | | |
|---|---|---|---|
| 7,834,029 | B2 | 11/2010 | Beight |
| 7,872,020 | B2 | 1/2011 | Mundla |

FOREIGN PATENT DOCUMENTS

| | | |
|---|---|---|
| CN | 100345852 C | 10/2007 |
| WO | WO-2014072517 A1 | 5/2014 |
| WO | WO-2016123573 A1 | 8/2016 |

(Continued)

OTHER PUBLICATIONS

Berge et al, Pharmaceutical Salts, Journal of Pharmaceutical of Science, Jan. 1977,66(No. 1), p. 1-19 (Year: 1977).*

(Continued)

*Primary Examiner* — Taylor V Oh
(74) *Attorney, Agent, or Firm* — Sterne, Kessler, Goldstein & Fox P.L.L.C.

(57) ABSTRACT

The present invention relates to a cocrystal of 2-(6-methyl-pyridine-2-yl)-3-yl-[6-amide-quinoline-4-yl]-5,6-dihydro-4H-pyrrole[1,2-b]pyrazole (Galunisertib or LY2157299) represented by formula (I) and a cocrystal former. Compared with the known solid form of Galunisertib, the cocrystal of the present invention has advantages in terms of stability, solubility, etc. The present invention also relates to a crystal form of the cocrystal, a preparation method therefor, a pharmaceutical composition thereof, and an application thereof in preparation of drugs for preventing and/or treating diseases relevant to TGF-β.

14 Claims, 9 Drawing Sheets

(56) References Cited

FOREIGN PATENT DOCUMENTS

WO    WO-2018170724 A    9/2018

OTHER PUBLICATIONS

International Search Report and Written Opinion in International Application No. PCT/CN2017/077459, State Intellectual Property Office of the P.R. China, China, dated Dec. 27, 2017, 7 pages.

\* cited by examiner

COCRYSTAL OF 2-(6-METHYL-PYRIDINE-2-YL)-3-YL-[6-AMIDE-QUINOLINE-4-YL]-5,6-DIHYDRO-4H-PYRROLE[1,2-B]PYRAZOLE, PREPARATION METHOD THEREFOR, AND PHARMACEUTICAL COMPOSITION

FIELD OF THE INVENTION

The present invention relates to the technical field of crystallization in pharmaceutical chemistry. Specifically, the present invention relates to the cocrystal of 2-(6-methyl-pyridin-2-yl)-3-(6-amido-quinolin-4-yl)-5,6-dihydro-4H-pyrrolo[1,2-b]pyrazole and succinic acid, the cocrystal of 2-(6-methyl-pyridin-2-yl)-3-(6-amido-quinolin-4-yl)-5,6-dihydro-4H-pyrrolo[1,2-b]pyrazole and fumaric acid, and their preparation methods, pharmaceutical compositions and uses.

BACKGROUND

Solid forms of drugs mainly include polymorph, salt, hydrate, solvate and cocrystal. Pharmaceutical cocrystal is the crystalline form combined an active pharmaceutical ingredient (API) with cocrystal former(s) (CCF) in a fixed stoichiometric ratio by weak interactions, in which the API could be in free form format or be in salt format. The weak interaction is defined as neither ionic bond interaction nor covalent bond interaction including such as hydrogen bond, van der Waals forces, π-π interactions and halogen bond. Cocrystal is a multi-component crystal, including binary cocrystal formed between two neutral solids and pluralistic cocrystal. Cocrystal can exists as polymorphs, or as hydrate or solvate. Reports have shown cocrystal has the ability to improve the crystal properties and chemical-physical properties of the drug.

2-(6-methyl-pyridin-2-yl)-3-(6-amido-quinolin-4-yl)-5,6-dihydro-4H-pyrrolo[1,2-b]pyrazole, another name LY2157299, is a transforming growth factor-beta (TGF-β) signaling inhibitor, English name Galunisertib. Its chemical structural formula is as following formula (I):

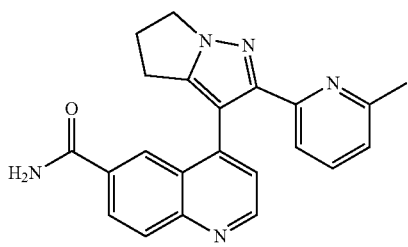

(I)

TGF-β includes three subtypes, TGF-β1, TGF-β2 and TGF-β3. It can affect the growth, differentiation and gene expression in many kinds of cells. TGF-β has close relationship with many diseases. As a singling inhibitor of TGF-β, LY2157299 can be used to treat cancers, pre-cancers, kidney diseases, fibrosis, and eye diseases. Patent CN100345852C disclosed LY2157299's preparation methods and mass data; U.S. Pat. No. 7,872,020B2 disclosed LY2157299 monohydrate's preparation method and its HNMR, mass data and XRPD data. The LY2157299 monohydrate described in U.S. Pat. No. 7,872,020B2 has disadvantages in low solubility and thermal phase stability issues.

In view of the disadvantages in the prior art, it is still necessary to develop new solid forms of LY2157299 including cocrystals in this field in order to meet the need in formulation in API solubility, stability and morphology.

SUMMARY OF THE INVENTION

In view of the disadvantages in the prior art, an objective of the present invention is to provide cocrystals of LY2157299, their crystalline forms, preparation methods, uses and pharmaceutical compositions thereof. The said cocrsytals in the present invention are stable crystalline solids, and should have one or more advantageous properties, especially in crystallinity, solubility, hygroscopicity, morphology, processibility and phase stability.

According to the purpose of the present invention, one aspect of the present invention is to provide succinate cocrystal of 2-(6-methyl-pyridin-2-yl)-3-(6-amido-quinolin-4-yl)-5,6-dihydro-4H-pyrrolo[1,2-b]pyrazole (referred as "succinate cocrystal" thereafter) and its crystalline form (referred as "succinate cocrystal form" thereafter) and its preparation methods.

The said succinate cocrystal contains 2-(6-methyl-pyridin-2-yl)-3-(6-amido-quinolin-4-yl)-5,6-dihydro-4H-pyrrolo[1,2-b]pyrazole and succinic acid, and 2-(6-methyl-pyridin-2-yl)-3-(6-amido-quinolin-4-yl)-5,6-dihydro-4H-pyrrolo[1,2-b]pyrazole and succinic acid form the cocrystals at a molar ratio of 1:0.5.

The said succinate cocrystal is a hydrate and contains one mole of water.

The succinate cocrystal, wherein the X-ray powder diffraction pattern of the succinate cocrystal form, using Cu-Kα radiation, expressed as 2θ angles, has the following characteristic peaks: $10.8°±0.2°$, $11.6°±0.2°$, $15.5°±0.2°$ and $20.2°±0.2°$.

In one preferred embodiment, the succinate cocrystal of the present invention, wherein the X-ray powder diffraction pattern of the succinate cocrystal form, using Cu-Kα radiation, expressed as 2θ angles, has one or more characteristic peaks in the following position: $12.3°±0.2°$, $16.8°±0.2°$, $18.0°±0.2°$, $21.3°±0.2°$, $21.7°±0.2°$, $22.0°±0.2°$, $24.6°±0.2°$ and $25.2°±0.2°$.

In another preferred embodiment, the succinate cocrystal of the present invention, wherein the X-ray powder diffraction pattern of the succinate cocrystal form, using Cu-Kα radiation, expressed as 2θ angles, has characteristic peaks in the following position: $12.3°±0.2°$, $16.8°±0.2°$, $18.0°±0.2°$, $21.3°±0.2°$, $21.7°±0.2°$, $22.0°±0.2°$, $24.6°±0.2°$ and $25.2°±0.2°$.

Non-restrictively, in one specific embodiment of the present invention, the X-ray powder diffraction pattern of the said succinate cocrystal form is shown in FIG. 5.

In another preferred embodiment, the succinate cocrystal of the present invention, wherein the Fourier-transform infrared spectrum of the succinate cocrystal form, has the following characteristic peaks: $3473\ cm^{-1}±2\ cm^{-1}$, $3141\ cm^{-1}±2\ cm^{-1}$, $1693\ cm^{-1}±2\ cm^{-1}$, $1580\ cm^{-1}±2\ cm^{-1}$, $1429\ cm^{-1}±2\ cm^{-1}$, $1322\ cm^{-1}±2\ cm^{-1}$, $1189\ cm^{-1}±2\ cm^{-1}$, $864\ cm^{-1}±2\ cm^{-1}$, $831\ cm^{-1}±2\ cm^{-1}$, $806\ cm^{-1}±2\ cm^{-1}$ and $609\ cm^{-1}±2\ cm^{-1}$.

Another aspect of the present invention is to provide preparation methods of single-crystal of the succinate cocrystal and its preparation method.

The single-crystal of the said succinate cocrystal form belongs to triclinic system, P1 space group and has the following single-crystal lattice parameters: $a=7.8\ Å±0.2\ Å$; $b=11.5\ Å±0.2\ Å$; $c=12.6\ Å±0.2\ Å$; $α=87.3°±0.2°$; $β=78.1°±0.2°$; $γ=89.2°±0.2°$.

Preferably, the single-crystal of the succinate cocrystal has the following lattice parameters: a=7.8 Å to 7.9 Å; b=11.4 Å to 11.5 Å; c=12.6 Å to 12.7 Å; α=87.3° to 78.4°; β=78.1° to 78.2° 1; γ=89.2° to 89.30°. More specifically, the single-crystal of the succinate cocrystal has the following lattice parameters: a=7.80 Å to 7.81 Å; b=11.45 Å to 11.46 Å; c=12.61 Å to 12.62 Å; α=87.33° to 78.34°; β=78.12° to 78.13°; γ=89.21° to 89.23°.

In a specific embodiment, the single-crystal of the succinate cocrystal has the following lattice parameters: a=7.807(4)Å; b=11.459(6)Å; c=12.613(7)Å; α=87.337(9)°; β=78.123(10)°; γ=89.220(10)°.

Moreover, in one specific embodiment the single-crystal of the succinate cocrystal form has the following atomic coordination.

| Atom | X | Y | Z | Atom | X | Y | Z |
|---|---|---|---|---|---|---|---|
| O(1) | 4305(2) | 8497(1) | 10421(1) | O(3) | 1340(2) | 2447(1) | 9671(1) |
| N(1) | 7141(2) | 6881(1) | 6487(1) | C(23) | 905(3) | 1466(2) | 9308(2) |
| N(2) | 5220(2) | 8255(1) | 4417(1) | C(24) | 348(3) | 547(1) | 10195(1) |
| N(3) | 3823(2) | 7829(1) | 4090(1) | O(4) | 2946(2) | −165(1) | 6855(1) |
| N(4) | 2557(2) | 4062(1) | 8070(1) | H(5A) | 4860 | 10030 | 9003 |
| N(5) | 4570(2) | 9377(1) | 8779(1) | H(5B) | 4504 | 9322 | 8111 |
| C(1) | 8690(3) | 5996(2) | 7784(2) | H(1A) | 7581 | 5639 | 8088 |
| C(2) | 8427(2) | 7002(2) | 7037(1) | H(1B) | 9200 | 6269 | 8356 |
| C(3) | 9428(2) | 8003(2) | 6927(2) | H(1C) | 9456 | 5432 | 7387 |
| C(4) | 9068(3) | 8920(2) | 6256(2) | H(3) | 10332 | 8059 | 7301 |
| C(5) | 7696(3) | 8830(2) | 5736(2) | H(4) | 9748 | 9592 | 6157 |
| C(6) | 6763(2) | 7791(1) | 5868(1) | H(5) | 7399 | 9451 | 5306 |
| C(7) | 5285(2) | 7620(1) | 5329(1) | H(10A) | 468 | 6506 | 4787 |
| C(8) | 3906(2) | 6785(1) | 5581(1) | H(10B) | 1818 | 5707 | 4032 |
| C(9) | 3023(2) | 6955(1) | 4737(1) | H(11A) | 1469 | 6921 | 2667 |
| C(10) | 1572(3) | 6497(2) | 4267(2) | H(11B) | 518 | 7855 | 3463 |
| C(11) | 1536(4) | 7348(3) | 3303(2) | H(12A) | 4037 | 7815 | 2465 |
| C(12) | 3202(3) | 8072(2) | 3092(2) | H(12B) | 2956 | 8897 | 2989 |
| C(13) | 3457(2) | 5887(1) | 6466(1) | H(14) | 3069 | 4607 | 5503 |
| C(14) | 3048(2) | 4776(1) | 6219(1) | H(15) | 2324 | 3169 | 6842 |
| C(15) | 2603(2) | 3904(1) | 7038(1) | H(17) | 2658 | 4695 | 9955 |
| C(16) | 2955(2) | 5150(1) | 8351(1) | H(18) | 3353 | 6459 | 10510 |
| C(17) | 2942(3) | 5315(2) | 9450(1) | H(20) | 3916 | 7841 | 7481 |
| C(18) | 3338(3) | 6370(2) | 9783(1) | H(3A) | 1741 | 2896 | 9157 |
| C(19) | 3727(2) | 7334(1) | 9038(1) | H(24A) | −552 | 870 | 10754 |
| C(20) | 3707(2) | 7197(1) | 7966(1) | H(24B) | 1341 | 338 | 10519 |
| C(21) | 3375(2) | 6099(1) | 7580(1) | H(4A) | 3594 | 308 | 6415 |
| C(22) | 4227(2) | 8458(2) | 9464(1) | H(4B) | 2214 | 217 | 7305 |
| O(2) | 962(2) | 1328(1) | 8357(1) | — | — | — | — |

In a preferred embodiment, the single-crystal of the succinate cocrystal form of the present invention is prepared. The preparation process includes the following steps: evaporating the succinate cocrystal solution (in methanol) using small hole method at room temperature to obtain the single-crystal. The "small hole" method places the solution in a container which has a singular hole with 2 mm in diameter and lets the solution evaporate at certain temperature.

Compared with the known LY2157299 monohydrate, the succinate cocrystal form of the present invention has the following beneficial properties:

(1) As shown in Comparative Example 1, the succinate cocrystal form of the present invention has an apparent water solubility of about 130 ug/mL, while the known LY2157299 monohydrate has an apparent water solubility less than 50 ug/mL, therefore the succinate cocrystal form of present invention has better apparent water solubility.

(2) The succinate cocrystal form has regular block like morphology, while the known LY2157299 monohydrate has needle like shape morphology, therefore the succinate cocrystal form of the present invention has better flowability and processibility.

(3) The succinate cocrystal form of the present invention remained its original crystalline form after 6 months of storage at 25° C./60% relative humidity, therefore it is stable.

The above advantageous properties of the succinate cocrystal form of the present invention show that, compared with the known LY2157299 monohydrate, the succinate cocrystal form of the present invention has many advantages and is more suitable for being used as the solid form of the active ingredient in pharmaceutical formulations. The known LY2157299 monohydrate has low water solubility which can affect the absorption and use of the dosage. The succinate cocrystal form of the present invention has higher solubility, therefore higher dissolution rate and better bioavailability. The succinate cocrystal form of the present invention also has good phase stability which can better ensure the quality, safety and stability of the active ingredients and formulations containing LY2157299.

The present invention provides a preparation method of the said succinate cocrystal form, wherein the preparation method is selected from any one of the following methods, comprising:

(1) adding a solvent to a mixture of LY2157299 monohydrate and succinic acid, grinding to dryness to obtain the succinate cocrystal form; the solvent is selected from the group consisting of methanol, acetonitrile, and water;

preferably, the LY2157299 monohydrate and succinic acid has a molar ratio of 1:0.5 to 1:1.2, more preferably 1:0.5 to 1:0.6; preferably, the weight to volume ratio of LY2157299 monohydrate to the solvent is from 80 mg:1 mL to 200 mg:1 mL, more preferably 80 mg:1 mL to 150 mg:1 mL;

preferably, the grinding temperature is 10 to 40° C., more preferably 10 to 30° C.;

(2) forming a suspension of a mixture of LY2157299 monohydrate and succinic acid in a solvent, stirring for crystallization, separating crystals and drying to obtain the said succinate cocrystal form; preferably, the solvent is selected from the group consisting of a $C_1$ to $C_4$ alcohol, ethyl acetate, and acetone;

preferably, the solvent is methanol;

preferably, the LY2157299 monohydrate and succinic acid has a molar ratio of 1:0.5 to 1:1.2, more preferably 1:1.0 to 1:1.2; preferably, the weight to volume ratio of LY2157299 monohydrate to the solvent is from 50 mg/mL to 100 mg/mL; preferably, the stirring temperature is from 10 to 40° C., more preferably 10 to 30° C.;

preferably, the stirring time is 4 to 16 hours.

According to the purpose of the present invention, the second aspect of the present invention is to provide fumarate cocrystal of 2-(6-methyl-pyridin-2-yl)-3-(6-amido-quinolin-4-yl)-5,6-dihydro-4H-pyrrolo[1,2-b]pyrazole (referred as "fumarate cocrystal" thereafter) and its crystalline form (referred as "fumarate cocrystal form" thereafter) and its preparation methods.

The said fumarate cocrystal contains 2-(6-methyl-pyridin-2-yl)-3-(6-amido-quinolin-4-yl)-5,6-dihydro-4H-pyrrolo[1,2-b]pyrazole and fumaric acid, and 2-(6-methyl-pyridin-2-yl)-3-(6-amido-quinolin-4-yl)-5,6-dihydro-4H-pyrrolo[1,2-b]pyrazole and fumaric acid form the cocrystals at a molar ratio of 1:0.5.

The fumarate cocrystal, wherein the X-ray powder diffraction pattern of the fumarate cocrystal form, using Cu-Kα radiation, expressed as 2θ angles, has the following characteristic peaks: 8.3°±0.2°, 9.8°±0.2°, 16.7°±0.2°.

In one preferred embodiment, the fumarate cocrystal of the present invention, wherein the X-ray powder diffraction pattern of the fumarate cocrystal form, using Cu-Kα radiation, expressed as 2θ angles, has one or more characteristic peaks in the following position: 15.5°±0.2°, 16.4°±0.2°, 23.4°±0.2°, 23.7°±0.2°, 24.2°±0.2°, 27.1°±0.2° and 28.3°±0.2°.

In another preferred embodiment, the fumarate cocrystal of the present invention, wherein the X-ray powder diffraction pattern of the fumarate cocrystal form, using Cu-Kα radiation, expressed as 2θ angles, has characteristic peaks in the following position: 15.5°±0.2°, 16.4°±0.2°, 23.4°±0.2°, 23.7°±0.2°, 24.2°±0.2°, 27.1°±0.2° and 28.3°±0.2°.

Non-restrictively, in one specific embodiment of the present invention, the X-ray powder diffraction pattern of the fumarate cocrystal form is shown in FIG. 12.

In another preferred embodiment, the fumarate cocrystal of the present invention, wherein the Fourier-transform infrared spectrum of fumarate cocrystal form, has the following characteristic peaks: 3350 $cm^{-1}$±2 $cm^{-1}$, 3153 $cm^{-1}$±2 $cm^{-1}$, 1681 $cm^{-1}$±2 $cm^{-1}$, 1588 $cm^{-1}$±2 $cm^{-1}$, 1395 $cm^{-1}$±2 $cm^{-1}$, 1320 $cm^{-1}$±2 $cm^{-1}$, 1149 $cm^{-1}$±2 $cm^{-1}$, 971 $cm^{-1}$±2 $cm^{-1}$, 870 $cm^{-1}$±2 $cm^{-1}$, 835 $cm^{-1}$±2 $cm^{-1}$, 747 $cm^{-1}$±2 $cm^{-1}$ and 634 $cm^{-1}$±2 $cm^{-1}$.

Another aspect of the present invention is to provide preparation methods of single-crystal of the fumarate cocrystal and its preparation method.

The single-crystal of the said fumarate cocrystal form belongs to triclinic system, P1 space group and when measured at 296K, it has the following single-crystal lattice parameters: a=8.6 Å±0.2 Å; b=11.7 Å±0.2 Å; c=12.2 Å±0.2 Å; α=99.9°±0.2°; β=102.3°±0.2°; γ=108.4°±0.2°.

Preferably, the single-crystal of the fumarate cocrystal form has the following lattice parameters: a=8.5 Å to 8.6 Å; b=11.6 Å to 11.7 Å; c=12.1 Å to 12.2 Å; α=99.9° to 100.0°; β=102.3° to 102.4°; γ=108.38° to 108.43°.

More specifically, the single-crystal of the fumarate cocrystal form has the following lattice parameters: a=8.57 Å to 7.8.58 Å; b=11.66 Å to 11.67 Å; c=12.17 Å to 12.18 Å; α=99.93° to 99.94°; β=102.31° to 102.32°; γ=108.40° to 108.41°.

In a specific embodiment, the single-crystal of the fumarate cocrystal form has the following lattice parameters: a=8.5700(12)Å; b=11.6640(16)Å; c=12.1714(16)Å; α=99.932(2)°; β=102.311(3)°; γ=108.401(3)°.

Moreover, in one specific embodiment the said single-crystal of the fumarate cocrystal form has the following atomic coordination.

| Atom | X | Y | Z | Atom | X | Y | Z |
|---|---|---|---|---|---|---|---|
| O(1) | 9074(2) | 10001(1) | 8545(1) | C(20) | 5544(2) | 7192(2) | 7199(1) |
| O(2) | 3086(2) | 4426(1) | 1305(1) | C(21) | 4375(2) | 6456(1) | 6107(1) |
| O(3) | 4952(2) | 6339(1) | 2254(1) | C(22) | 8308(2) | 8878(2) | 8428(2) |
| N(1) | 2478(2) | 8092(2) | 6938(2) | C(23) | 4285(2) | 5359(2) | 1371(1) |
| N(2) | 1076(2) | 5909(2) | 8558(1) | C(24) | 5143(2) | 5470(2) | 431(1) |
| N(3) | 657(2) | 4672(2) | 8166(1) | H(3A) | 4537 | 6185 | 2784 |
| N(4) | 3883(2) | 5883(1) | 4010(1) | H(5A) | 9195 | 8746 | 9959 |
| N(5) | 8505(2) | 8321(1) | 9283(1) | H(5B) | 7943 | 7534 | 9160 |
| C(1) | 3158(6) | 9657(3) | 5870(4) | H(1A) | 3110 | 8943 | 5318 |
| C(2) | 2968(4) | 9313(2) | 6987(3) | H(1B) | 4240 | 10325 | 6025 |
| C(3) | 3297(4) | 10196(3) | 8003(4) | H(1C) | 2244 | 9923 | 5558 |
| C(4) | 3120(4) | 9829(3) | 8981(3) | H(3) | 3639 | 11040 | 8018 |
| C(5) | 2669(3) | 8578(2) | 8955(2) | H(4) | 3301 | 10415 | 9664 |
| C(6) | 2363(2) | 7737(2) | 7911(2) | H(5) | 2573 | 8308 | 9622 |
| C(7) | 1880(2) | 6390(2) | 7816(1) | H(10A) | 1534 | 2678 | 7016 |
| C(8) | 1984(2) | 5433(2) | 6955(1) | H(10B) | −31 | 2629 | 6023 |
| C(9) | 1141(2) | 4336(2) | 7215(2) | H(11A) | −1822 | 2246 | 7119 |
| C(10) | 570(3) | 2951(2) | 6847(2) | H(11B) | −450 | 1854 | 7883 |
| C(11) | −636(5) | 2536(3) | 7587(3) | H(12A) | −1322 | 3708 | 8708 |
| C(12) | −271(3) | 3638(2) | 8585(2) | H(12B) | 432 | 3587 | 9300 |
| C(13) | 2719(2) | 5549(1) | 5970(1) | H(14) | 783 | 4131 | 4760 |
| C(14) | 1813(2) | 4782(2) | 4870(1) | H(15) | 1802 | 4443 | 3189 |
| C(15) | 2437(2) | 4977(2) | 3920(1) | H(17) | 6786 | 7671 | 4522 |
| C(16) | 4890(2) | 6622(1) | 5097(1) | H(18) | 8558 | 8905 | 6304 |
| C(17) | 6470(2) | 7552(2) | 5191(1) | H(20) | 5256 | 7074 | 7877 |
| C(18) | 7535(2) | 8276(2) | 6252(2) | H(24) | 5920 | 6248 | 462 |
| C(19) | 7092(2) | 8077(2) | 7277(1) | — | — | — | — |

In a preferred embodiment, the single-crystal of fumarate cocrystal form of the present invention is prepared. The preparation process includes the following steps: evaporating the fumarate cocrystal solution (in methanol) using small hole method at room temperature to obtain the single-crystal. The "small hole" method places the solution in a container which has a singular hole with 2 mm in diameter and lets the solution evaporate at certain temperature.

Compared with the known LY2157299 monohydrate, the fumarate cocrystal form of the present invention has the following beneficial properties:

(1) As shown in Comparative Example 1, the fumarate cocrystal form of the present invention has an apparent water solibility of about 330 ug/mL, while the known LY2157299 monohydrate has an apparent water solubility less than 50 ug/mL, therefore the fumarate cocrystal form of present invention has better apparent water solubility.

(2) The fumarate cocrystal form has regular block like morphology, while the known LY2157299 monohydrate has needle like shape morphology, therefore the fumarate cocrystal form of the present invention has better flowability and processibility.

(3) The fumarate cocrystal form of the present invention remained its original crystalline form after 6 months of storage at 25° C./60% relative humidity, therefore it is stable.

The above advantageous properties of the fumarate cocrystal form of the present invention show that, compared with the known LY2157299 monohydrate, the fumarate cocrystal form of the present invention has many advantages and is more suitable for being used as the solid form of the active ingredient in pharmaceutical formulations. The known LY2157299 monohydrate has low water solubility which can affect the absorption and use of the dosage. The fumarate cocrystal form of the present invention has higher solubility, therefore higher dissolution rate and better bioavailability. The fumarate cocrystal form of the present invention also has good phase stability which can better ensure the quality, safety and stability of the active ingredients and formulations containing LY2157299.

The present invention provides a preparation method of the fumarate cocrystal form, wherein the preparation method is selected from any one of the following methods, comprising:

(1) adding a solvent to a mixture of LY2157299 monohydrate and fumaric acid, grinding to dryness to obtain the fumarate cocrystal form; the solvent is selected from the group consisting of methanol, acetonitrile, and water;

preferably, the weight to volume ratio of the mixture to the solvent is from 60 mg:1 mL to 160 mg:1 mL;

preferably, the LY2157299 monohydrate and fumaric acid has a molar ratio of 1:0.5 to 1:1.2, more preferably 1:0.5 to 1:0.6;

preferably, the grinding temperature is 10 to 40° C., more preferably 10 to 30° C.;

(2) forming a suspension of a mixture of LY2157299 monohydrate and fumaric acid in a solvent, stirring for crystallization, separating crystals and drying to obtain the said fumarate cocrystal form; preferably, the solvent is selected from the group consisting of a $C_1$ to $C_4$ alcohol, ethyl acetate, and acetone;

preferably, the solvent is methanol;

preferably, the LY2157299 monohydrate and fumaric acid has a molar ratio of 1:0.5 to 1:1.2, more preferably 1:1.0 to 1:1.2;

preferably, the weight to volume ratio of LY2157299 monohydrate to the solvent is from 50 mg/mL to 100 mg/mL;

preferably, the stirring temperature is from 10 to 40° C., more preferably 10 to 30° C.;

preferably, the stirring time is 4 to 16 hours.

In the preparation methods of the present invention, LY2157299 starting material can be known LY2157299, its crystalline forms or its amorphous form, such as but not limited to LY2157299 monohydrate prepared by referencing the methods described in examples of patent document U.S. Pat. No. 7,872,020B2. This document is incorporated herein by reference in its entirety.

The terms used in this invention include:

The $C_1$ to $C_4$ alcohol includes methanol, ethanol, n-propanol, isopropanol, n-butanol, 2-butanol and tert-butanol.

The "room temperature" refers to 10 to 30° C.

The "stirring" may be performed by routine methods in the field, such as magnetic stirring or mechanical stirring. The stirring speed is 50-1800 r/min, preferably 300-900 r/min.

The "grinding" may be performed by routine methods in the field, such as grinding using a mortar and pestle.

The "separation" may be performed by routine methods in the field, such as filtration, centrifugation, or volatilization. The preferred method is vacuum filtration, generally at a pressure less than atmospheric pressure at room temperature, preferably less than 0.09 MPa.

The said "drying" may be performed by routine methods in the field, such as room temperature drying, blast drying or vacuum drying. Drying instruments and methods are unrestricted, may be fume hood, blast oven, spray drying, fluidized bed drying or vacuum oven, the pressure may be atmospheric pressure or less than atmospheric pressure, preferably less than 0.09 MPa. Drying temperature can be 10 to 40° C., drying time is 10 to 72 hr, preferably 2 to 24 hr, more preferably 2 to 8 hr.

The "crystalline form" in the present invention is confirmed by the X-ray powder diffraction pattern, having a unique ordered molecular arrangement or configuration within the crystal lattice. It is known to those skilled in the field that experimental errors of X-ray diffraction depend on instrument conditions, sample preparation and sample purity. The 2θ angle of the peaks in the X-ray powder diffraction pattern usually varies slightly due to the difference in the instrument and sample. The differences in peak position may vary by 1°, 0.8°, 0.5°, 0.3°, 0.1° 2θ, depending on different instruments and samples, and usually ±0.2° in differences are allowed. The relative intensities of peaks may change with the change of samples, sample preparation and other experimental conditions; therefore, the order of peak intensities should not be regarded as the only or the determining factor. Due to the effect of experimental factors including sample height, peak position may shift; generally, a small amount of peak shifting is acceptable experimental error. Hence, it is easily understood for those skilled in the field that any crystalline forms having the same or similar X-ray powder diffraction pattern as that of the crystalline form of corresponding forms in the present invention should be within the scope of the present invention. "Pure crystalline form" refers to a pure crystalline form confirmed by X-ray powder diffraction.

The crystalline form of the cocrystals of LY2157299 of the present invention is substantially pure and substantially free of any other crystalline or amorphous forms. When "substantially pure" in the present invention referring to a new crystalline form, it means that the new crystalline form comprises at least 80% by weight of the compound present, more preferably at least 90% by weight, especially at least 95% by weight, in particular at least 99% by weight.

According to the purpose of the present invention, the present invention provided is a pharmaceutical composition, the uses of the said composition in treating or preventing diseases related to TGF-β; the diseases related to TGF-β include cancers, pre-cancers, kidney diseases, pulmonary fibrosis and eye disease.

The said composition comprises a therapeutically and/or preventively effective amount of one or more novel crystalline forms of LY2157299 cocrystals of the present invention or LY2157299 salts, and at least one pharmaceutically acceptable carrier; wherein the cocrystals of LY2157299 include LY2157299 succinate cocrystal and LY2157299 fumarate cocrystal. Optionally, the pharmaceutical composition may also include other acceptable active ingredients, such as other TGF-β inhibitors, anti-proliferation or anti-cancer drugs.

According to the present invention, the method for treating a human include administering TGF-β inhibitors. The TGF-β inhibitor can be made into oral, rectal, local and parental such as injection dosage forms, including tablets, powders, capsules, lozenges, emulsions, creams, syrups, sublinguals, small medicine bags, flat capsules, elixirs gels, suspensions, injectable solutions, aerosols, ointments, suppository, or a combination of two or many such forms.

The cocrystal of LY2157299 and its composition in the present invention can be administered to patients in single dose or separate dose at 0.5 mg/kg to 50 mg/kg. The single dose can have 0.5 mg to about 1000 mg of the said compound. When administered orally, the composition can be administered as pills or capsules containing 0.5 mg to 500 mg of the active ingredient, especially containing 0.5 mg, 1 mg, 5 mg, 10 mg, 15 mg, 20 mg, 25 mg, 50 mg, 75 mg, 80 mg/100 mg, 120 mg, 150 mg, 175 mg, 200 mg and 500 mg, and in a daily dose of 0.5 mg/kg to 40 mg/kg. The actual dose of the active ingredient should depends on many factors, include severity of the disease, patient age, age, physical conditions, gender, the potency and metabolism, administration route, therefore the above dose selection has no meanings to limit the scope of the present invention.

The pharmaceutical compound can contain at least one cocrystal designated in this invention, mixed with pharmaceutically acceptable excipients to make a composition, and use capsules, small medicine bags, flat capsules, paper or other absorbable container or shelfs or disposable container such as ampules to pack or seal. The excipients can be solid, semi-solid, or liquid. The pharmaceutical composition can use excipients such as starch, sugar, syrup, sorbitol, mannitol, glycol, wax, clay, calcium silicate, silicon dioxide, polyvinylpyrrolidone, calcium phosphate, cocoa butter, ester, oil, Alginate, gel, methyl cellulose, microcrystalline cellulose, lubricant, binder and disintegrant.

The preferred dosage forms are pills, powders, capsules, injectables (solutions), creams, ointments and aerosols.

FIGURE DESCRIPTIONS

FIG. 1 is the XRPD plot of LY2157299 monohydrate prepared according to U.S. Pat. No. 7,872,020B2.

FIG. 2 is the DSC plot of LY2157299 monohydrate prepared according to U.S. Pat. No. 7,872,020B2.

FIG. 3 is the TGA plot of LY2157299 monohydrate prepared according to U.S. Pat. No. 7,872,020B2.

FIG. 4 is the PLM plot of LY2157299 monohydrate prepared according to U.S. Pat. No. 7,872,020B2.

EXAMPLES

The following examples will help to further understand the present invention, but are not intended to limit the contents of the present invention.

Instruments and Characterization Methods:

X-ray powder diffraction (XRPD): performed on Bruker D8 Advance diffractometer. Samples were tested at room temperature. Testing conditions: 2θ scan range 3-40°, step size 0.02°, and speed 0.2 s/step.

Single-crystal diffractometer: ruker SMART APEX II, 4K CCD detector. Detection parameters: ambient temperature 296 K, enhanced Mo light source, the wavelength 0.71 Å. Data analysis software is Bruker SHELXTL.

Differential thermal analysis data were collected on TA Instruments Q200 DSC. Method: A sample of 1 to 10 mg was placed in an aluminum pan with a pin-holed lid, and the sample was heated from room temperature to 200° C. at a heating rate of 10° C./min under the protection of dry nitrogen purge at 40 mL/min.

Thermogravimetric analysis data were collected on TA Instruments Q500 TGA. Method: A sample of 5 to 15 mg was placed in a platinum pan, using High Resolution™, the sample was heated from room temperature to 350° C. at a heating rate of 10° C./min under the protection of dry nitrogen purge at 40 mL/min.

1H Nuclear magnetic resonance spectrum (1H-NMR) data were collected on Bruker Avance II DMX 500 MHz nuclear magnetic resonance spectrometer. Method: place 1 mg to 5 mg sample and dissolve it into a nuclear magnetic sample tube with 0.5 mL deuterated reagent for detection.

The PLM used is model)CR-500E, optical lens 10×, subject lens 10×. Place some samples in a slide, add one drop of silica oil, place a cover slip and observe.

IR data was collected using Bruker Tensor 27, ATR, range 600-4000 cm$^{-1}$.

Unless particularly specified, all reagents used in the Examples were commercially available.

Unless particularly specified, all Examples were operated at room temperature.

IR data was collected using Bruker Tensor 27, ATR, range 600-4000 cm$^{-1}$.

Preparation Example 1

Preparing LY2157299 Monohydrate

LY2157299 monohydrate was obtained according to Example 1 in U.S. Pat. No. 7,872,020B2.

$^1$H-NMR (CDCl$_3$): δ=9.0 ppm (d, 4.4 Hz, 1H); 8.23-8.19 ppm (m, 2H); 8.315 ppm (dd, 1.9 Hz, 8.9 Hz, 1H); 7.455 ppm (d, 4.4 Hz, 1H); 7.364 ppm (t, 7.7 Hz, 1H); 7.086 ppm (d, 8.0 Hz, 1H); 6.969 ppm (d, 7.7 Hz, 1H); 6.022 ppm (m, 1H); 5.497 ppm (m, 1H); 4.419 ppm (d, 7.3 Hz, 2H); 2.999 ppm (m, 2H); 2.770 ppm (p, 7.2 Hz, 7.4 Hz, 2H); 2.306 ppm (s, 3H); 1.817 ppm (m, 2H). MS ES$^+$: 370.2; Exact: 369.16.

Figure 1:
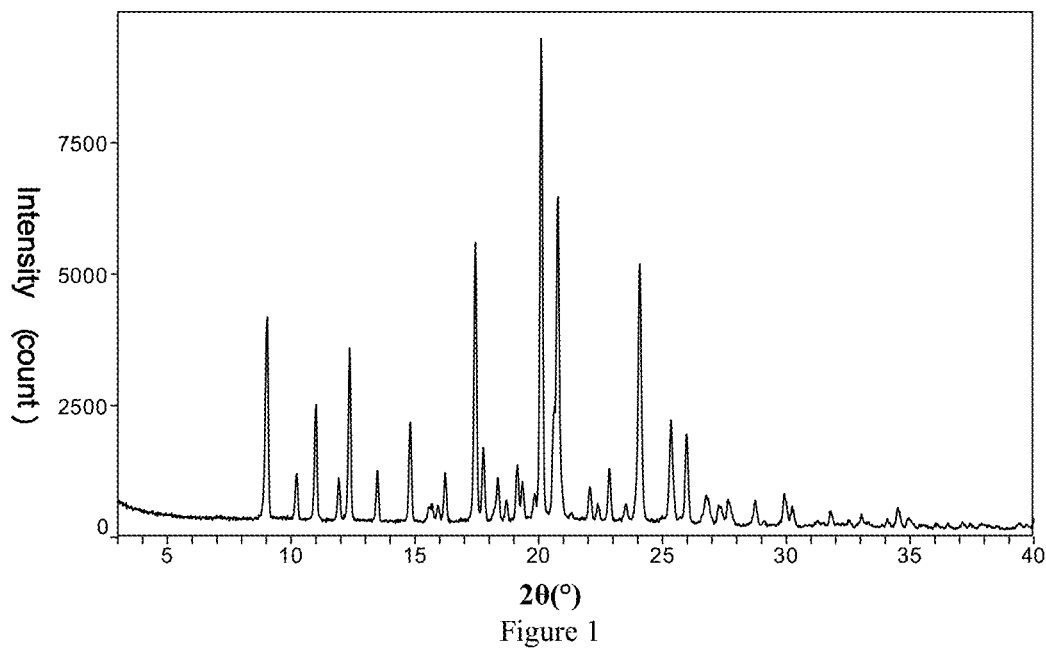

Its XRPD plot is shown in FIG. 1, and its peak lists are accordant with that of the monohydrate of U.S. Pat. No. 7,872,020B2.

Figure 2:
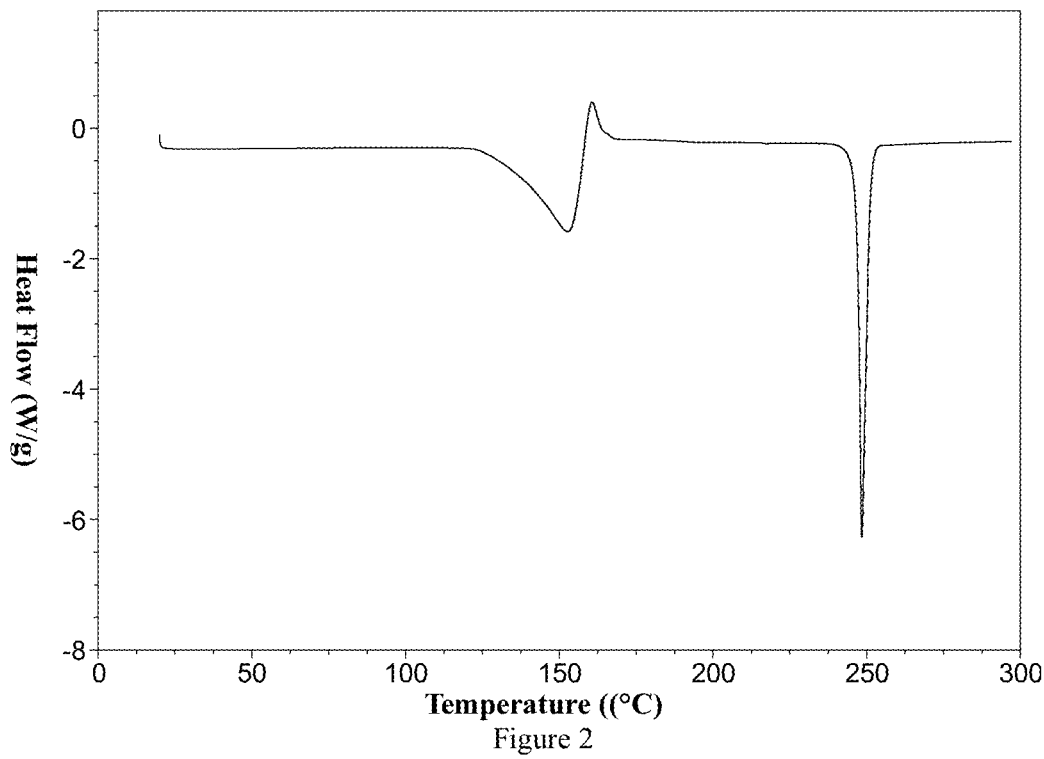

Its DSC plot is shown in FIG. 2: dehydrated at 133° C. and stated phase transition, after phase transition it melted at 247° C.

Figure 3:
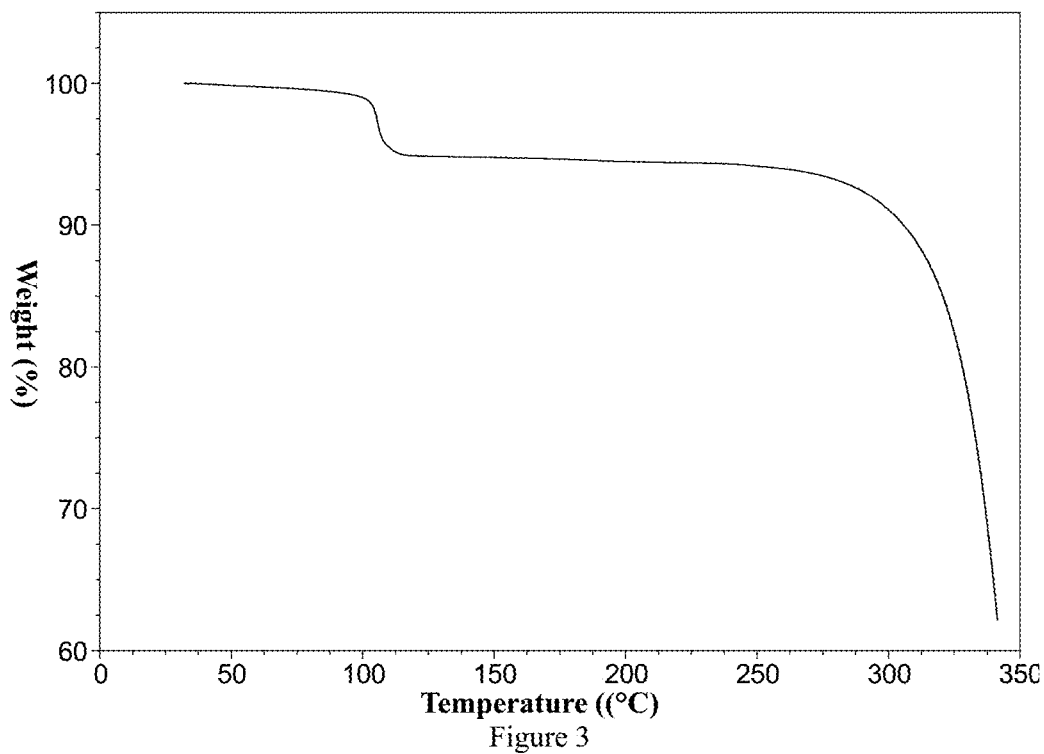
Figure 4:
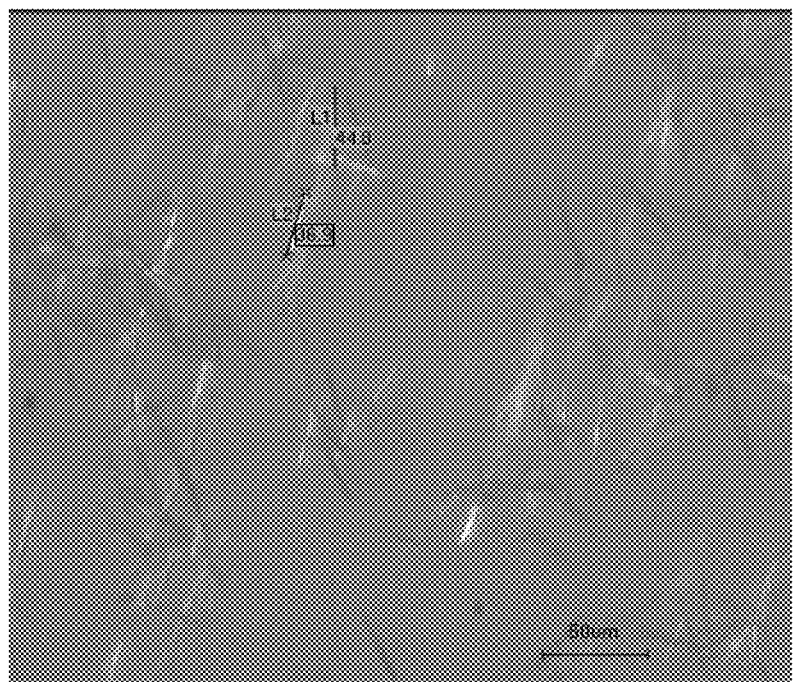

Its TGA plot is shown in FIG. 3: 4.7% step-wise weight loss at 80° C.~120° C., eq. to about one mole of water, decomposes at 323° C.

Figure 5:
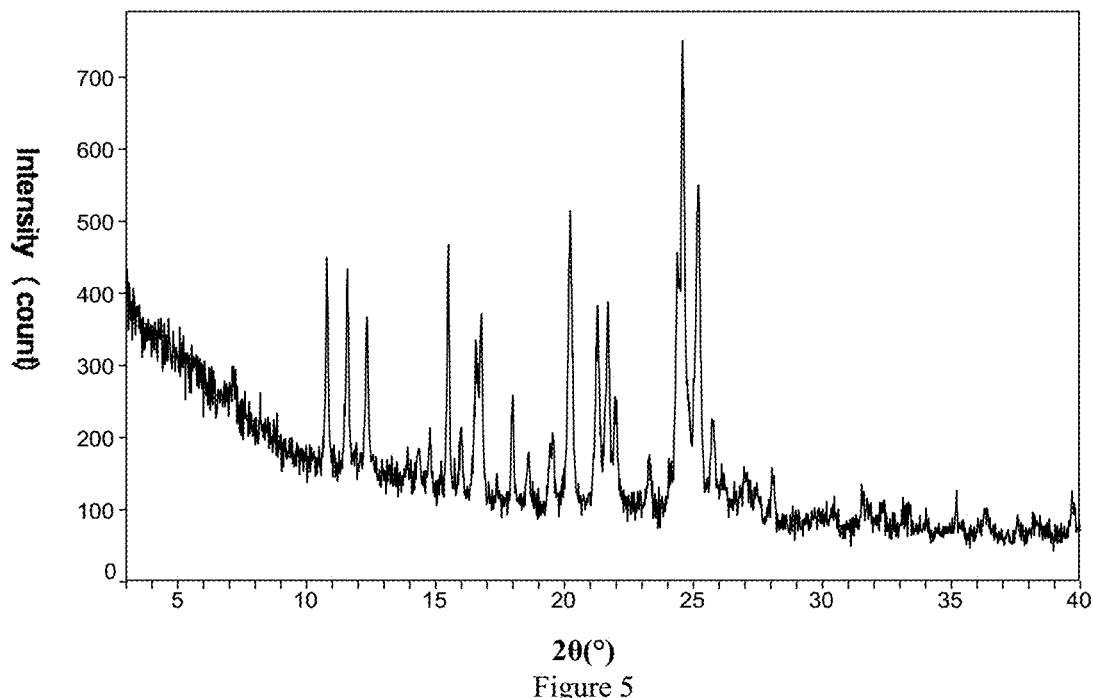
FIG. 5 is the XRPD plot of the succinate cocrystal form of the present invention.

Its PLM plot is shown in FIG. 5: needle like tiny crystals.

Example 1

Took 192 mg of LY2157299 monohydrate and mixed with 29.3 mg succinic acid, added 2.4 mL of methanol, ground at 40° C. to dryness, and obtained 190 mg succinate cocrystal, yield 86%.

Its XRPD plot is shown in FIG. 5, showing it is a crystalline material; its peak position, d-spacing value and the relative intensity of the X-ray diffraction pattern of the succinate cocrystal are shown in Table 1.

Figure 6:
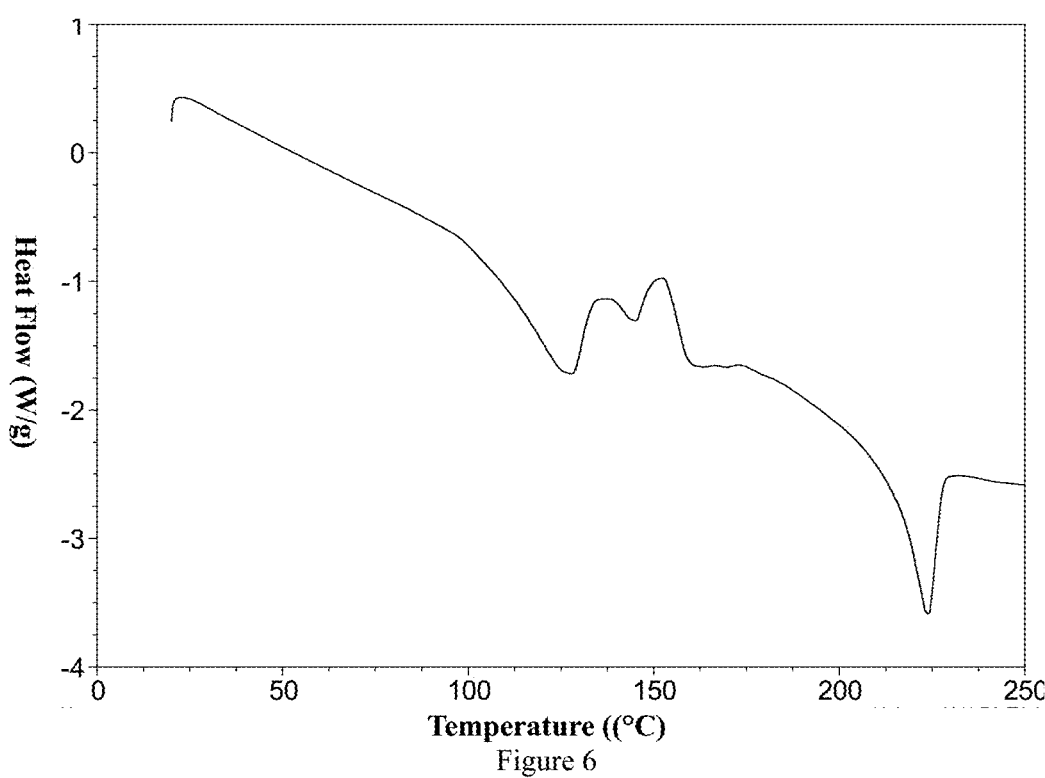
FIG. 6 is the DSC plot of the succinate cocrystal form of the present invention.

Its DSC thermogram is shown in FIG. 6, showing a dehydration peak at 100° C. to 130° C.

Figure 7:
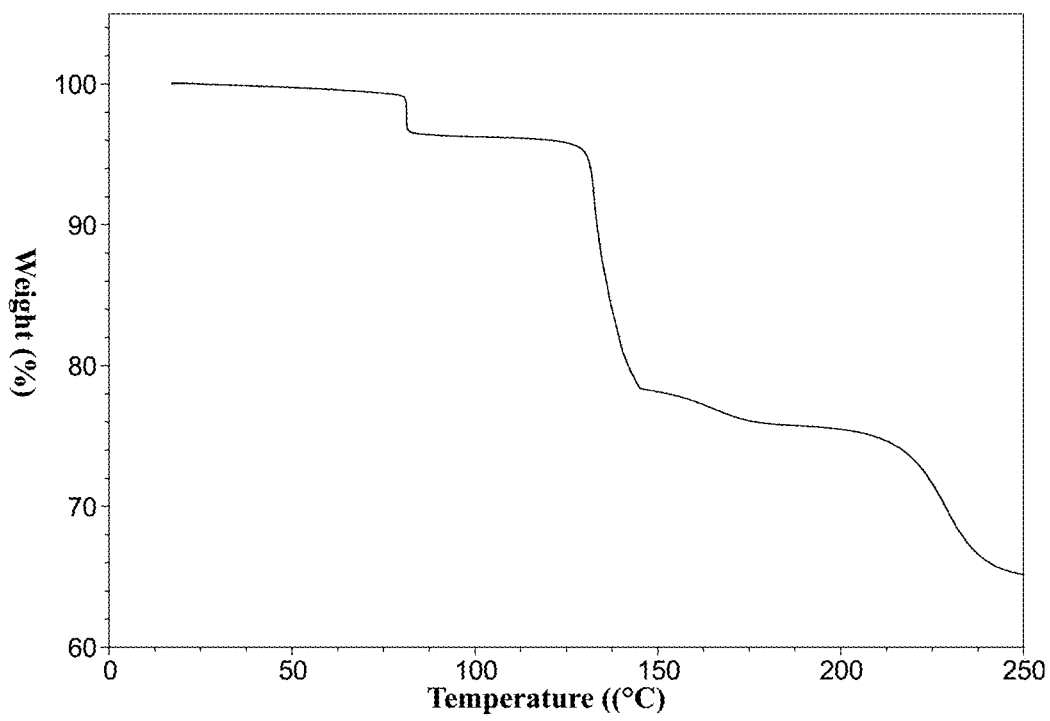
FIG. 7 is the TGA plot of the succinate cocrystal form of the present invention.

Its TGA thermogram is shown in FIG. 7, showing dehydration temperation at approximately 80° C.

Figure 10:
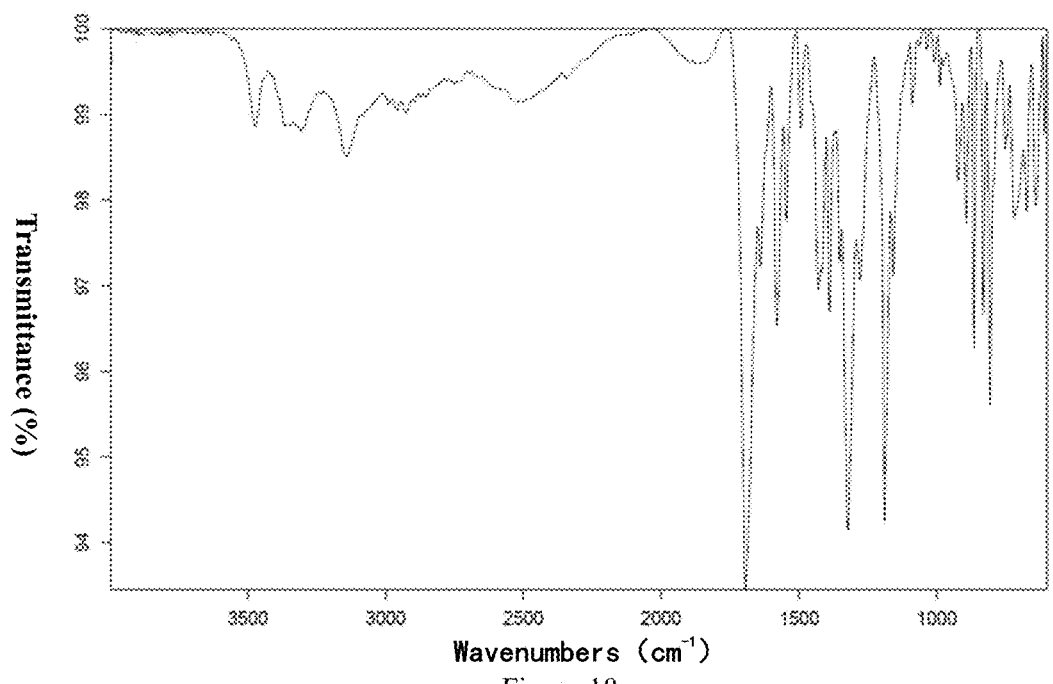
FIG. 10 is the IR spectrum of the succinate cocrystal form of the present invention.

Its IR spectrum is shown in FIG. 10.

TABLE 1

The peak position, d-spacing value and the relative intensity of the X-ray diffraction pattern of the succinate cocrystal.

| Peak 2θ | d-Spacing | Relative Intensity I % |
|---|---|---|
| 7.1° | 12.39 Å | 10.3 |
| 10.8° | 8.19 Å | 46.1 |
| 11.6° | 7.63 Å | 43.3 |
| 12.3° | 7.17 Å | 33.1 |
| 13.9° | 6.36 Å | 6.8 |
| 14.3° | 6.17 Å | 7.8 |
| 14.8° | 5.98 Å | 12.7 |
| 15.5° | 5.71 Å | 54.2 |
| 16.0° | 5.54 Å | 13.9 |
| 16.8° | 5.28 Å | 40.4 |
| 17.4° | 5.10 Å | 6.3 |

TABLE 1-continued

The peak position, d-spacing value and the relative intensity of the X-ray diffraction pattern of the succinate cocrystal.

| Peak 2θ | d-Spacing | Relative Intensity I % |
|---|---|---|
| 18.0° | 4.92 Å | 24.1 |
| 18.6° | 4.76 Å | 11.4 |
| 19.5° | 4.54 Å | 15.1 |
| 20.2° | 4.38 Å | 64.0 |
| 21.3° | 4.17 Å | 43.3 |
| 21.7° | 4.09 Å | 44.5 |
| 22.0° | 4.04 Å | 23.1 |
| 23.3° | 3.81 Å | 11.4 |
| 24.4° | 3.65 Å | 51.7 |
| 24.6° | 3.62 Å | 100.0 |
| 25.2° | 3.53 Å | 65.1 |
| 25.7° | 3.46 Å | 15.1 |
| 27.1° | 3.29 Å | 8.7 |
| 27.5° | 3.25 Å | 5.7 |
| 28.0° | 3.18 Å | 11.7 |

Example 2

Took some of the succinate cocrystal prepared in Example 1, placed in methanol to form a solution, and evaporated using the small-hole method at room temperature to obtain the single-crystal of the succinate cocrystal form.

Its lattice parameter is shown in Table 2 and its atomic coordination is shown in Table 3.

TABLE 2

The lattice parameter of the single crystal of the succinate cocrystal.

| Lattice parameters | |
|---|---|
| Structural formula | LY2157299·0.5HOOC(CH$_2$)$_2$COOH·H$_2$O |
| Molecular formula | C$_{24}$H$_{24}$N$_5$O$_4$ |
| Molecular weight (g/mol) | 446.48 |
| Crystal system | monoclinic system |
| Space group | P 1 |
| Temperature/K | 296 |
| a/Å | 7.807(4) |
| b/Å | 11.459(6) |
| c/Å | 12.613(7) |
| α/° | 87.337(9) |
| β/° | 78.123(10) |
| γ/° | 89.220(10) |
| Z | 2 |
| V/Å$^3$ | 1103.0(10) |
| D$_{calc}$/g cm$^{-3}$ | 1.344 |

In Table 2, a, b, c represent axial lengths of the unit cell, α, β, γ represent dihedral angles, Z represents the number of molecules of LY2157299·0.5 HOOC(CH$_2$)$_2$COOH·H$_2$O in each unit cell, V represents cell volume, D$_{calc}$ represents cell density.

Single-crystal analytical parameters: residual factor R1=0.1004, weighted R value wR$^2$=0.1617, goodness of fit GooF (S)=1.023, S value is almost 1. The parameters indicate that the single-crystal data is reasonable.

Figure 8:
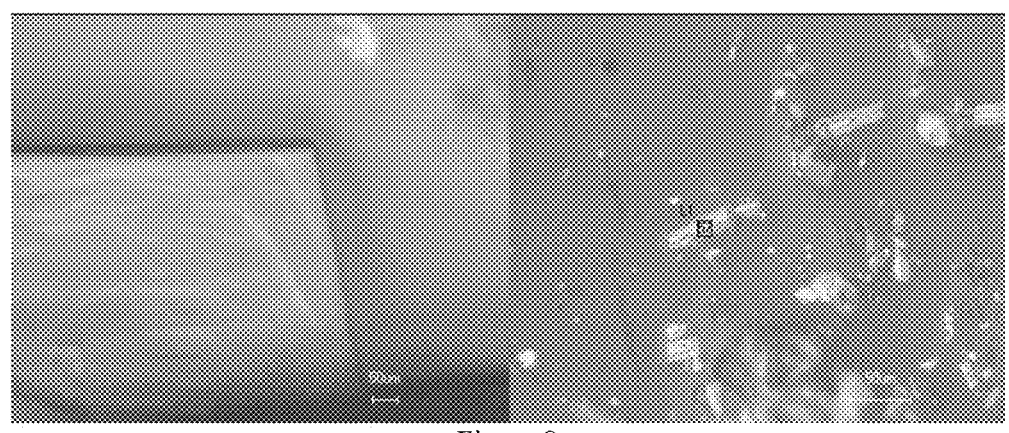
FIG. 8 is the PLM plot of the succinate cocrystal form of the present invention.

The PLM plot of the single-crystal of the succinate cocrystal is shown in FIG. 8, showing big block like crystals.

Figure 9:
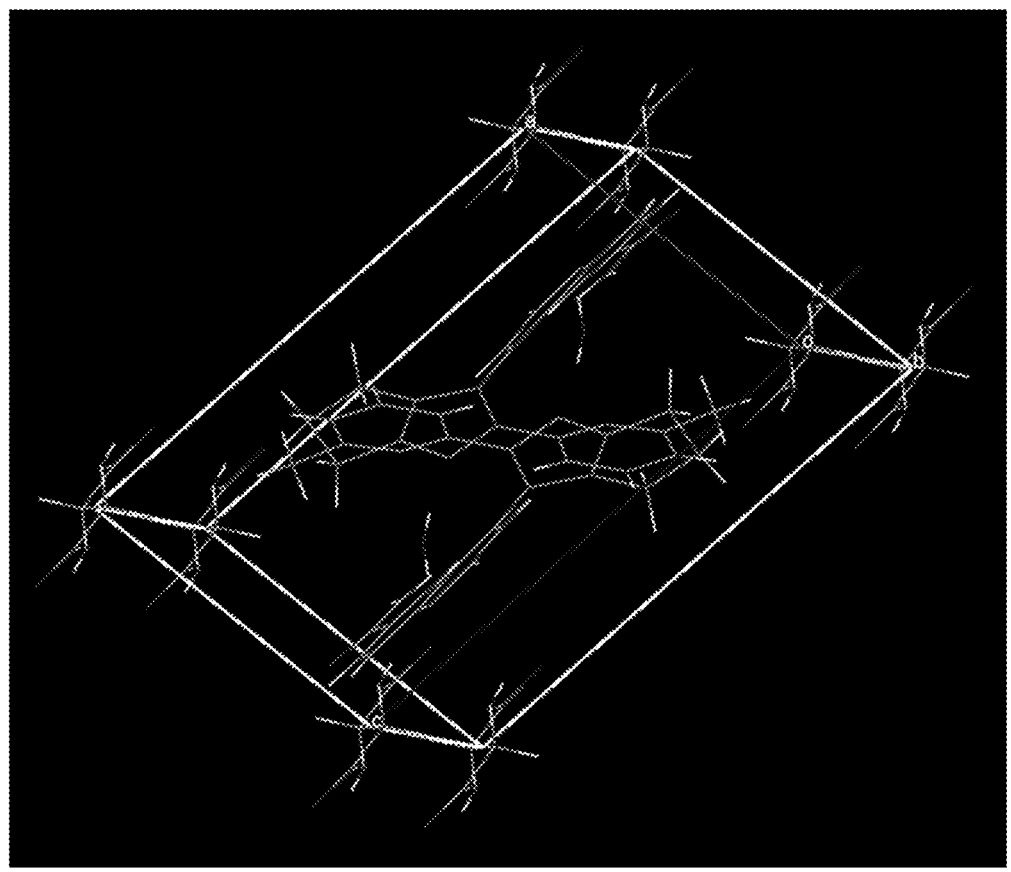
FIG. 9 is the molecular structure diagram of the single-crystal of the succinate cocrystal form of the present invention.

Molecular structure diagram of the single-crystal of the succinate cocrystal is shown in FIG. 9, indicating that LY2157299 molecule and water molecule are inside of the unit cell, the succinic acid molecule is on the top corner of the unit cell; and the single-crystal molecule consists of one LY2157299 molecule, one water molecule and half succinic acid molecule.

Figure 11:
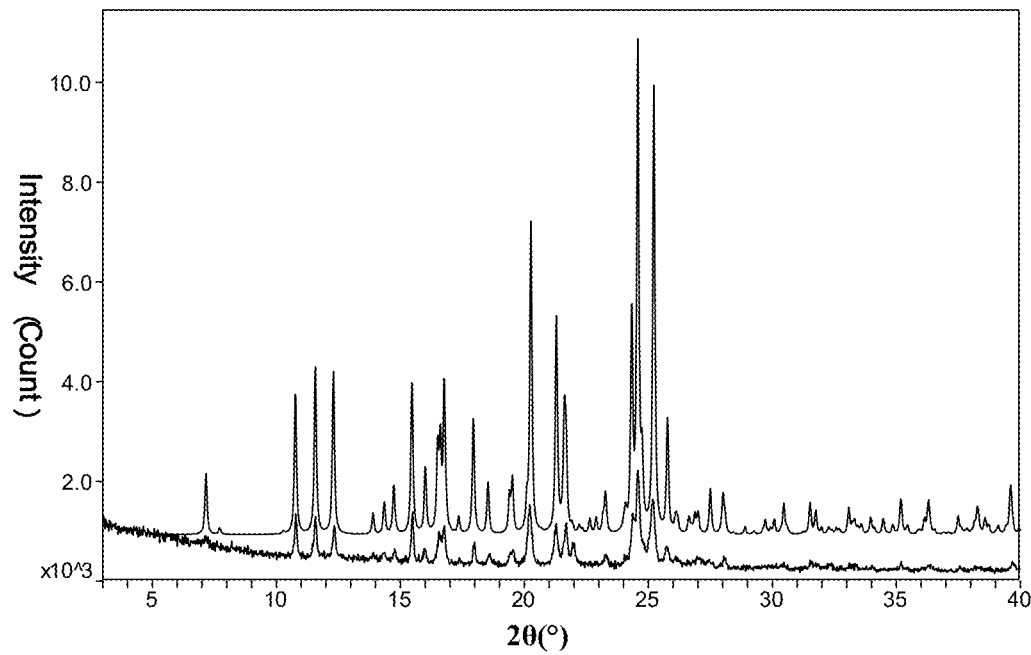
FIG. 11 is the is the XRPD pattern of the succinate cocrystal form in the present invention (top) and the simulated XRD pattern from the single-crystal data of the succinate cocrystal(bottom).

The XRPD comparison diagram shown in FIG. 11 contains the simulated XRD patterns based on single-crystal dada (bottom) and the actual measured XRPD pattern of the succinate cocrystal (top), showing that both are essentially identical.

TABLE 3

The atomic coordination of the single-crystal of the succinate cocrystal.

| Atom | X | Y | Z | Atom | X | Y | Z |
|---|---|---|---|---|---|---|---|
| O(1) | 4305(2) | 8497(1) | 10421(1) | O(3) | 1340(2) | 2447(1) | 9671(1) |
| N(1) | 7141(2) | 6881(1) | 6487(1) | C(23) | 905(3) | 1466(2) | 9308(2) |
| N(2) | 5220(2) | 8255(1) | 4417(1) | C(24) | 348(3) | 547(1) | 10195(1) |
| N(3) | 3823(2) | 7829(1) | 4090(1) | O(4) | 2946(2) | −165(1) | 6855(1) |
| N(4) | 2557(2) | 4062(1) | 8070(1) | H(5A) | 4860 | 10030 | 9003 |
| N(5) | 4570(2) | 9377(1) | 8779(1) | H(5B) | 4504 | 9322 | 8111 |
| C(1) | 8690(3) | 5996(2) | 7784(2) | H(1A) | 7581 | 5639 | 8088 |
| C(2) | 8427(2) | 7002(2) | 7037(1) | H(1B) | 9200 | 6269 | 8356 |
| C(3) | 9428(2) | 8003(2) | 6927(2) | H(1C) | 9456 | 5432 | 7387 |
| C(4) | 9068(3) | 8920(2) | 6256(2) | H(3) | 10332 | 8059 | 7301 |
| C(5) | 7696(3) | 8830(2) | 5736(2) | H(4) | 9748 | 9592 | 6157 |
| C(6) | 6763(2) | 7791(1) | 5868(1) | H(5) | 7399 | 9451 | 5306 |
| C(7) | 5285(2) | 7620(1) | 5329(1) | H(10A) | 468 | 6506 | 4787 |
| C(8) | 3906(2) | 6785(1) | 5581(1) | H(10B) | 1818 | 5707 | 4032 |
| C(9) | 3023(2) | 6955(1) | 4737(1) | H(11A) | 1469 | 6921 | 2667 |
| C(10) | 1572(3) | 6497(2) | 4267(2) | H(11B) | 518 | 7855 | 3463 |
| C(11) | 1536(4) | 7348(3) | 3303(2) | H(12A) | 4037 | 7815 | 2465 |
| C(12) | 3202(3) | 8072(2) | 3092(2) | H(12B) | 2956 | 8897 | 2989 |
| C(13) | 3457(2) | 5887(1) | 6466(1) | H(14) | 3069 | 4607 | 5503 |
| C(14) | 3048(2) | 4776(1) | 6219(1) | H(15) | 2324 | 3169 | 6842 |
| C(15) | 2603(2) | 3904(1) | 7038(1) | H(17) | 2658 | 4695 | 9955 |
| C(16) | 2955(2) | 5150(1) | 8351(1) | H(18) | 3353 | 6459 | 10510 |
| C(17) | 2942(3) | 5315(2) | 9450(1) | H(20) | 3916 | 7841 | 7481 |
| C(18) | 3338(3) | 6370(2) | 9783(1) | H(3A) | 1741 | 2896 | 9157 |
| C(19) | 3727(2) | 7334(1) | 9038(1) | H(24A) | −552 | 870 | 10754 |
| C(20) | 3707(2) | 7197(1) | 7966(1) | H(24B) | 1341 | 338 | 10519 |
| C(21) | 3375(2) | 6099(1) | 7580(1) | H(4A) | 3594 | 308 | 6415 |
| C(22) | 4227(2) | 8458(2) | 9464(1) | H(4B) | 2214 | 217 | 7305 |
| O(2) | 962(2) | 1328(1) | 8357(1) | — | — | — | — |

Example 3

Took 45 mg of LY2157299 monohydrate and mixed with 8.3 mg succinic acid, added 0.3 mL of methanol, ground at 10° C. to dryness, and obtained 46 mg succinate cocrystal form, yield 89%.

Example 4

Took 30 mg of LY2157299 monohydrate and mixed with 9.1 mg succinic acid, added 0.15 mL of acetonitrile, ground at 10° C. to dryness, and obtained 29 mg succinate cocrystal form, yield 84%.

Example 5

Took 15 mg of LY2157299 monohydrate and mixed with 5.5 mg succinic acid, added 0.15 mL of methanol, ground at 40° C. to dryness, and obtained 14 mg succinate cocrystal form, yield 81%.

Example 6

Took 50 mg of LY2157299 monohydrate and mixed with 18.3 mg succinic acid, added 0.5 mL of methanol to form a suspension, stirred at 30° C. for 4 hrs, filtered, dried at room temperature for 1 hr and obtained 47 mg succinate cocrystal form, yield 82%.

Example 7

Took 30 mg of LY2157299 monohydrate and mixed with 4.6 mg succinic acid, added 0.6 mL of ethanol to form a suspension, stirred at 10° C. for 16 hrs, filtered, dried at room temperature for 1 hr and obtained 25 mg succinate cocrystal form, yield 72%.

Example 8

Took 20 mg of LY2157299 monohydrate and mixed with 7.3 mg succinic acid, added 0.25 mL of isopropanol to form a suspension, stirred at 10° C. for 8 hrs, filtered, dried at room temperature for 1 hr and obtained 18 mg succinate cocrystal form, yield 78%.

Example 9

Took 50 mg of LY2157299 monohydrate and mixed with 15.2 mg succinic acid, added 1 mL of n-butanol to form a suspension, stirred at 20° C. for 10 hrs, filtered, dried at room temperature for 1 hr and obtained 44 mg succinate cocrystal form, yield 76%.

Example 10

Took 50 mg of LY2157299 monohydrate and mixed with 8 mg succinic acid, added 0.5 mL of ethyl acetate to form a suspension, stirred at 40° C. for 4 hrs, filtered, dried at room temperature for 1 hr and obtained 43 mg succinate cocrystal form, yield 75%.

Example 11

Took 50 mg of LY2157299 monohydrate and mixed with 11 mg succinic acid, added 0.63 mL of acetone to form a suspension, stirred at 40° C. for 4 hrs, filtered, dried at room temperature for 1 hr and obtained 41 mg succinate cocrystal form, yield 71%.

XRPD patterns, DSC plots, TGA plots (not shown) of the samples prepared in Examples 3 to 11 are the same as or similar to that of the sample prepared in Example 1, indicating the cocrystals obtained in Examples 3 to 11 are the same as that of Example 1.

Example 12

Took 15 mg of LY2157299 monohydrate and mixed with 2.2 mg fumaric acid, added 0.25 mL of methanol, ground at 10° C. to dryness, and obtained 14 mg fumarate cocrystal, yield 85%.

Figure 12:
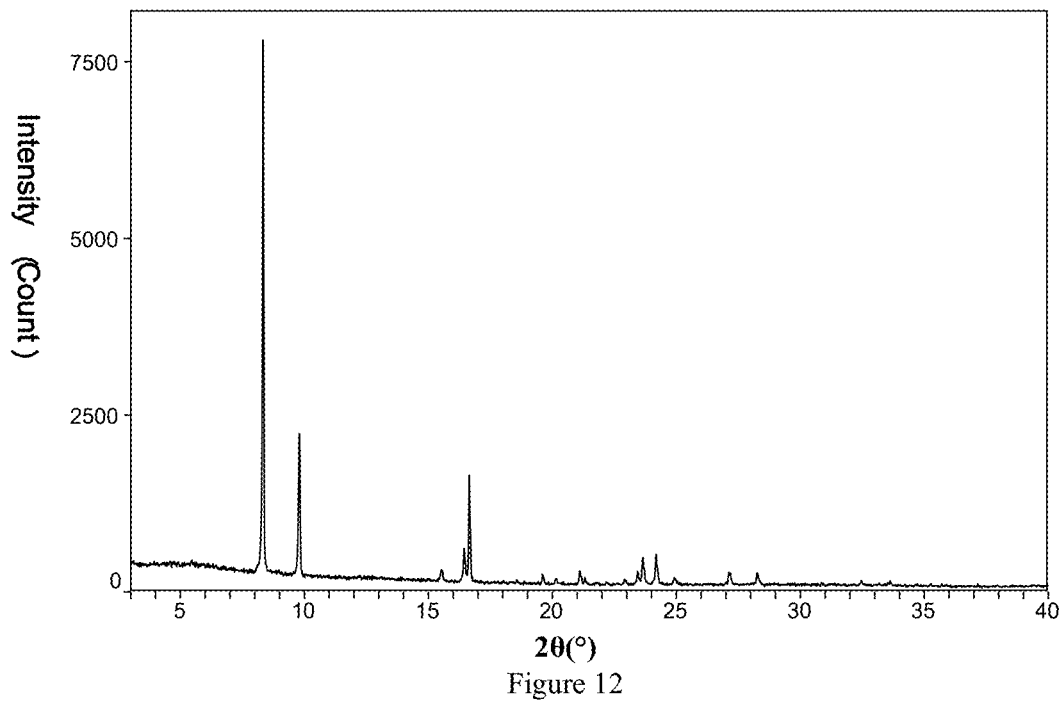
FIG. 12 is the XRPD plot of the fumarate cocrystal form of the present invention.

Its XRPD plot is shown in FIG. 12, showing it is a crystalline material; its peak position, d-spacing value and the relative intensity of the X-ray diffraction pattern of the fumarate cocrystal are shown in Table 4.

Figure 13:
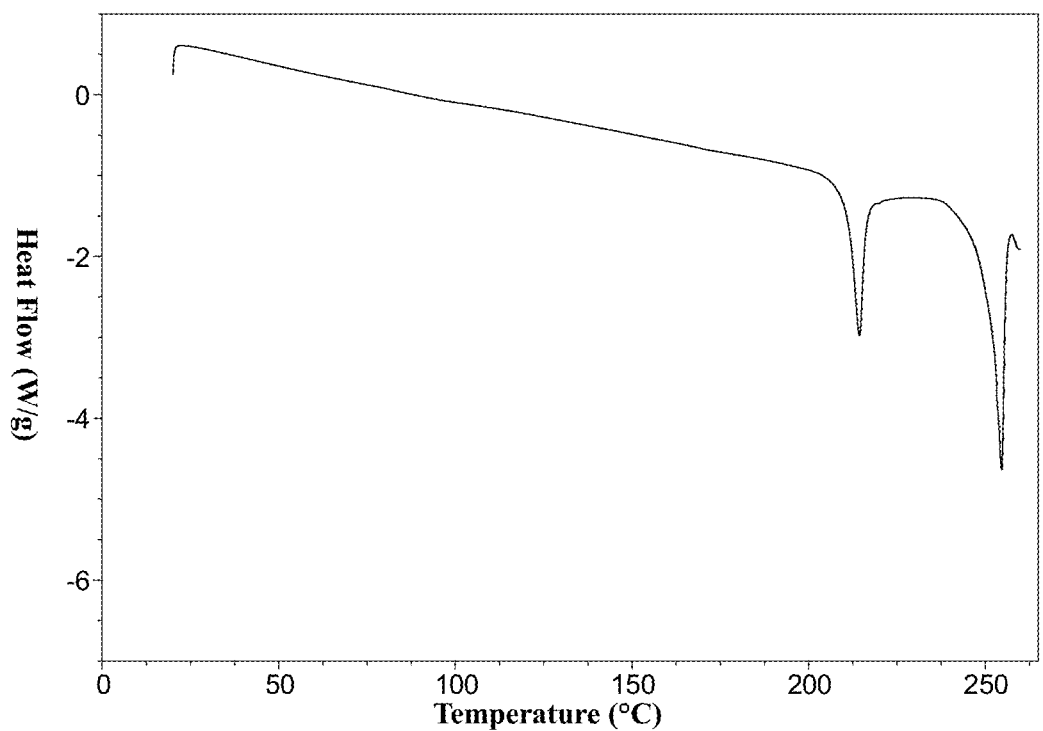
FIG. 13 is the DSC plot of the fumarate cocrystal form of the present invention.

Its DSC thermogram is shown in FIG. 13, showing a melting point at approximately 211° C.

Figure 14:
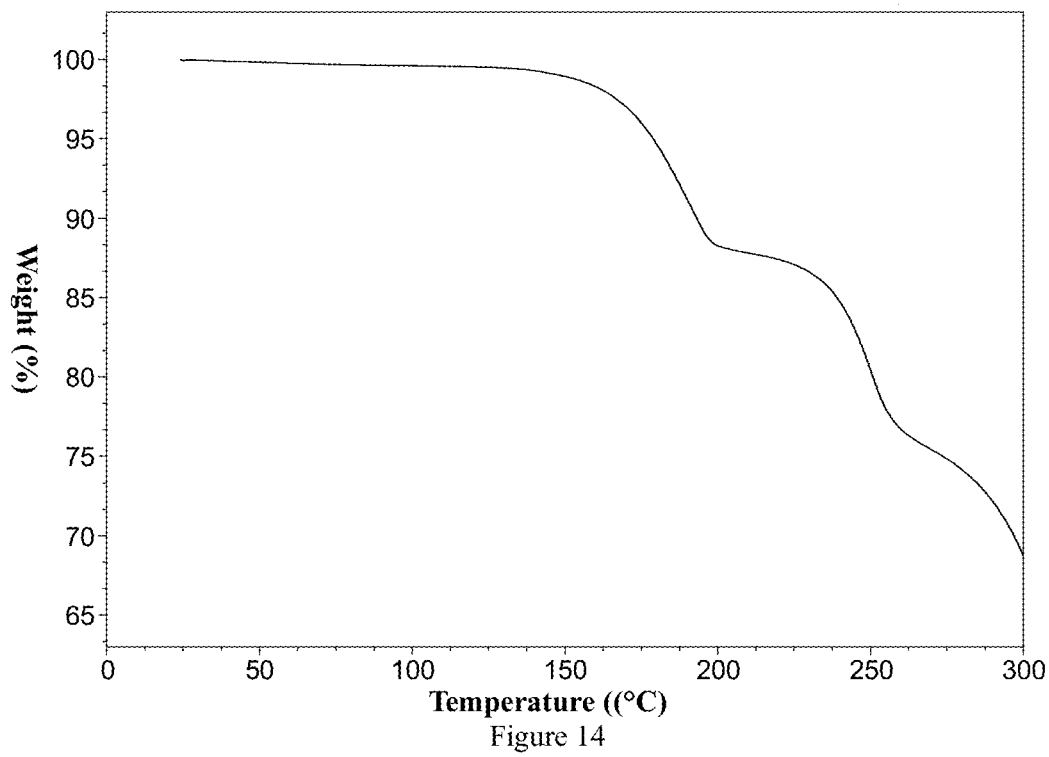
FIG. 14 is the TGA plot of the fumarate cocrystal form of the present invention.

Its TGA thermogram is shown in FIG. 14, showing it is an anhydrous material.

Figure 17:
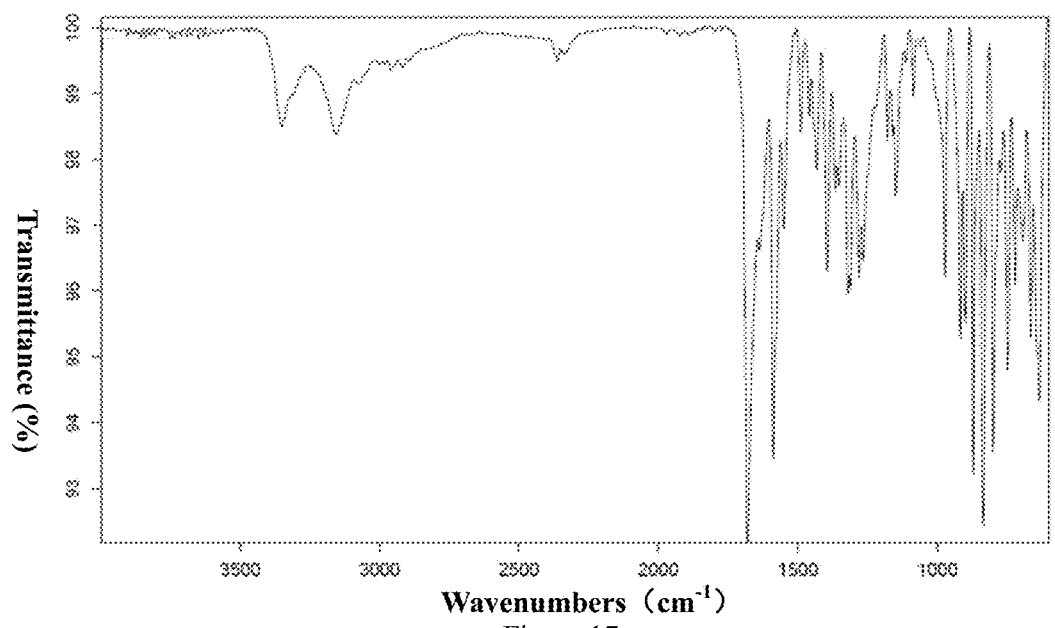
FIG. 17 is the IR spectrum of the fumarate cocrystal form of the present invention.

Its IR spectrum is shown in FIG. 17.

TABLE 4

The peak position, d-spacing value and the relative intensity of the X-ray diffraction pattern of the fumarate cocrystal.

| Peak Position 2θ | d-Spacing | Relative Intensity I % |
|---|---|---|
| 8.3° | 10.59 Å | 100.0 |
| 9.8° | 9.02 Å | 26.5 |
| 15.5° | 5.70 Å | 2.1 |
| 16.4° | 5.39 Å | 6.2 |
| 16.7° | 5.32 Å | 20.1 |
| 18.6° | 4.77 Å | 0.7 |
| 19.6° | 4.52 Å | 1.7 |
| 20.2° | 4.40 Å | 0.9 |
| 21.1° | 4.20 Å | 2.4 |
| 21.3° | 4.16 Å | 1.2 |
| 22.9° | 3.88 Å | 1.0 |
| 23.4° | 3.79 Å | 2.4 |
| 23.7° | 3.76 Å | 5.0 |
| 24.2° | 3.68 Å | 5.6 |
| 24.9° | 3.57 Å | 1.3 |
| 27.1° | 3.28 Å | 2.3 |
| 28.3° | 3.15 Å | 2.2 |

Example 13

Took some of the fumarate cocrystal prepared in Example 12, placed in methanol to form a solution, and evaporated using the small-hole method at room temperature to obtain the single-crystal of the fumarate cocrystal form.

Its lattice parameter is shown in Table 5 and its atomic coordination is shown in Table 6.

TABLE 5

The lattice parameter of the single-crystal of the fumarate cocrystal.

| Lattice parameters | |
|---|---|
| Structural formula | LY2157299•0.5 HOOC(CH)$_2$COOH |
| Molecular formula | $C_{24}H_{21}N_5O_3$ |
| Molecular weight (g/mol) | 427.46 |
| Crystal system | Triclinic |
| Space group | P 1 |
| Temperature/K | 296 |
| a/Å | 8.5700(12) |
| b/Å | 11.6640(16) |
| c/Å | 12.1714(16) |
| α/° | 99.932(2) |
| β/° | 102.311(3) |
| γ/° | 108.401(3) |
| Z | 2 |
| V/Å$^3$ | 1089.5(3) |
| $D_{calc}$/g cm$^{-3}$ | 1.303 |

In table 5, a, b, c represent axial lengths of the unit cell, α, β, γ represent dihedral angles, Z represents the number of molecules of LY2157299·0.5 HOOC(CH)$_2$COOH in each unit cell, V represents cell volume, $D_{calc}$ represents cell density.

Single-crystal analytical parameters are as following: residual factor R1=0.1145, weighted R value wR$^2$=0.1606, goodness of fit GooF (S)=1.008, and S value is almost 1. The parameters indicate that the single-crystal data is reasonable.

Figure 15:
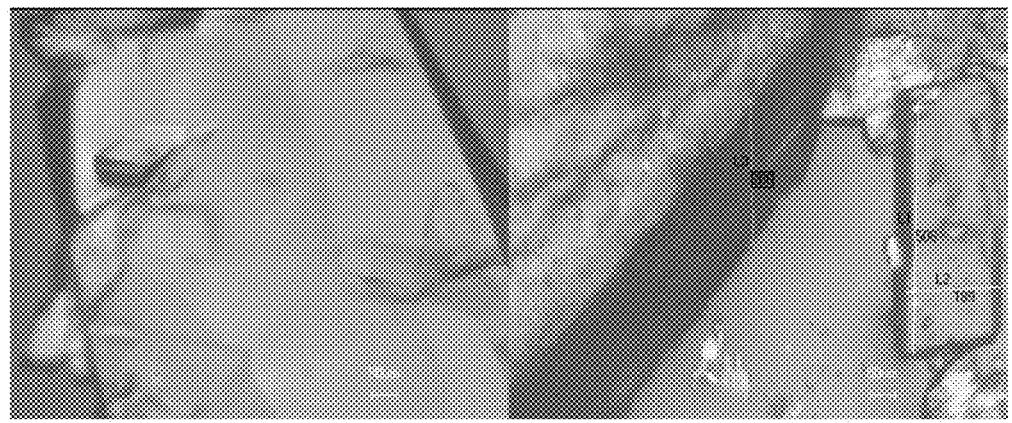
FIG. 15 is the PLM plot of the fumarate cocrystal form of the present invention.

The PLM plot of the single-crystal of the fumarate cocrystal is shown in FIG. 15, showing big block like crystals.

Figure 16:
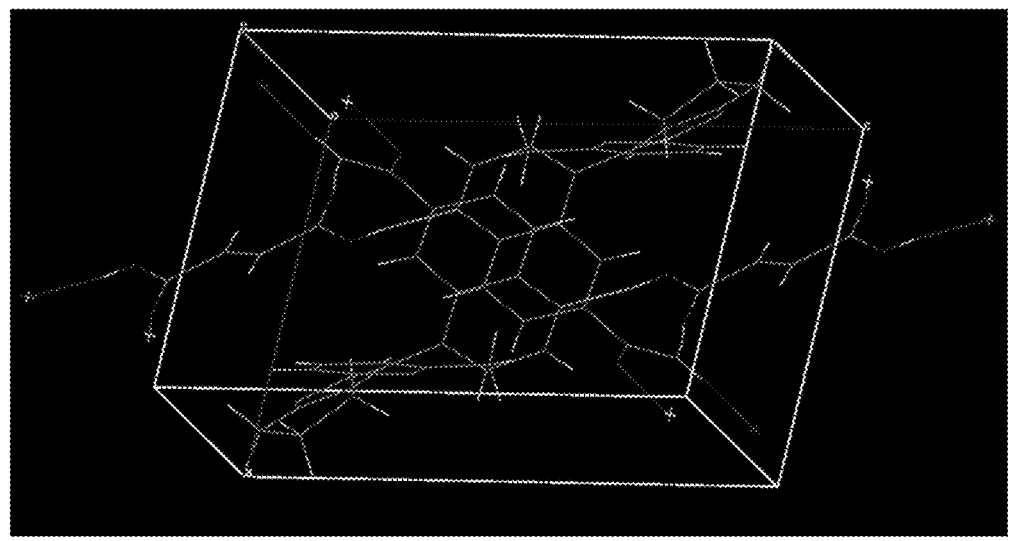
FIG. 16 is the molecular structure diagram of the single-crystal of the fumarate cocrystal form of the present invention.

Molecular structure diagram of the single-crystal of the fumarate cocrystal is shown in FIG. 16, indicating that LY2157299 molecule is inside of the unit cell, the fumaric acid molecule is on the plane; and the single-crystal molecule consists of one LY2157299 molecule and half fumaric acid molecule.

Figure 18:
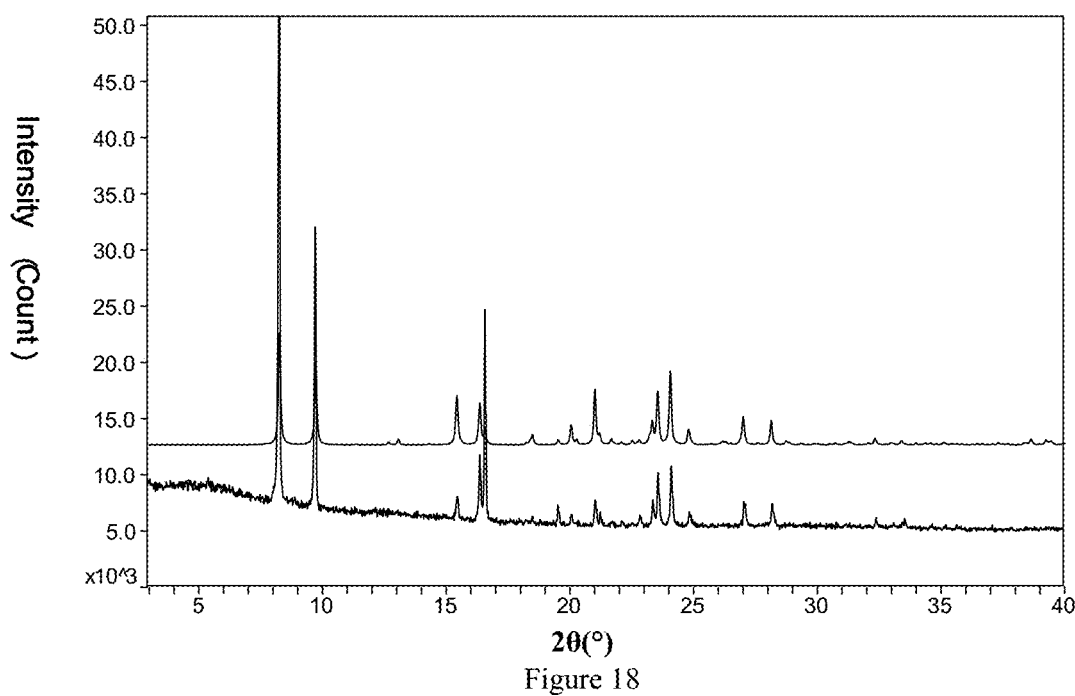
FIG. 18 is the is the XRPD pattern of the fumarate cocrystal form in the present invention (top) and the simulated XRD pattern from the single-crystal data of the fumarate cocrystal(bottom).

The XRPD comparison diagram shown in FIG. 18 contains the simulated XRD patterns based on single-crystal dada (bottom) and the actual measured XRPD pattern of the fumarate cocrystal (top), showing that both are essentially identical.

TABLE 6

The atomic coordination of the single-crystal of the fumarate cocrystal.

| Atom | X | Y | Z | Atom | X | Y | Z |
|---|---|---|---|---|---|---|---|
| O(1) | 9074(2) | 10001(1) | 8545(1) | C(20) | 5544(2) | 7192(2) | 7199(1) |
| O(2) | 3086(2) | 4426(1) | 1305(1) | C(21) | 4375(2) | 6456(1) | 6107(1) |
| O(3) | 4952(2) | 6339(1) | 2254(1) | C(22) | 8308(2) | 8878(2) | 8428(2) |
| N(1) | 2478(2) | 8092(2) | 6938(2) | C(23) | 4285(2) | 5359(2) | 1371(1) |
| N(2) | 1076(2) | 5909(2) | 8558(1) | C(24) | 5143(2) | 5470(2) | 431(1) |
| N(3) | 657(2) | 4672(2) | 8166(1) | H(3A) | 4537 | 6185 | 2784 |
| N(4) | 3883(2) | 5883(1) | 4010(1) | H(5A) | 9195 | 8746 | 9959 |

TABLE 6-continued

The atomic coordination of the single-crystal of the fumarate cocrystal.

| Atom | X | Y | Z | Atom | X | Y | Z |
|---|---|---|---|---|---|---|---|
| N(5) | 8505(2) | 8321(1) | 9283(1) | H(5B) | 7943 | 7534 | 9160 |
| C(1) | 3158(6) | 9657(3) | 5870(4) | H(1A) | 3110 | 8943 | 5318 |
| C(2) | 2968(4) | 9313(2) | 6987(3) | H(1B) | 4240 | 10325 | 6025 |
| C(3) | 3297(4) | 10196(3) | 8003(4) | H(1C) | 2244 | 9923 | 5558 |
| C(4) | 3120(4) | 9829(3) | 8981(3) | H(3) | 3639 | 11040 | 8018 |
| C(5) | 2669(3) | 8578(2) | 8955(2) | H(4) | 3301 | 10415 | 9664 |
| C(6) | 2363(2) | 7737(2) | 7911(2) | H(5) | 2573 | 8308 | 9622 |
| C(7) | 1880(2) | 6390(2) | 7816(1) | H(10A) | 1534 | 2678 | 7016 |
| C(8) | 1984(2) | 5433(2) | 6955(1) | H(10B) | −31 | 2629 | 6023 |
| C(9) | 1141(2) | 4336(2) | 7215(2) | H(11A) | −1822 | 2246 | 7119 |
| C(10) | 570(3) | 2951(2) | 6847(2) | H(11B) | −450 | 1854 | 7883 |
| C(11) | −636(5) | 2536(3) | 7587(3) | H(12A) | −1322 | 3708 | 8708 |
| C(12) | −271(3) | 3638(2) | 8585(2) | H(12B) | 432 | 3587 | 9300 |
| C(13) | 2719(2) | 5549(1) | 5970(1) | H(14) | 783 | 4131 | 4760 |
| C(14) | 1813(2) | 4782(2) | 4870(1) | H(15) | 1802 | 4443 | 3189 |
| C(15) | 2437(2) | 4977(2) | 3920(1) | H(17) | 6786 | 7671 | 4522 |
| C(16) | 4890(2) | 6622(1) | 5097(1) | H(18) | 8558 | 8905 | 6304 |
| C(17) | 6470(2) | 7552(2) | 5191(1) | H(20) | 5256 | 7074 | 7877 |
| C(18) | 7535(2) | 8276(2) | 6252(2) | H(24) | 5920 | 6248 | 462 |
| C(19) | 7092(2) | 8077(2) | 7277(1) | — | — | — | — |

Example 14

Took 72 mg of LY2157299 monohydrate and mixed with 13 mg fumaric acid, added 0.45 mL of methanol, ground at 30° C. to dryness, and obtained 69 mg fumarate cocrystal form, yield 87%.

Example 15

Took 30 mg of LY2157299 monohydrate and mixed with 10.8 mg fumaric acid, added 0.2 mL of acetonitrile, ground at 10° C. to dryness, and obtained 26 mg fumarate cocrystal form, yield 79%.

Example 16

Took 15 mg of LY2157299 monohydrate and mixed with 4.5 mg fumaric acid, added 0.2 mL of water, ground at 40° C. to dryness, and obtained 12 mg fumarate cocrystal form, yield 72%.

Example 17

Took 50 mg of LY2157299 monohydrate and mixed with 7.6 mg fumaric acid, added 0.5 mL of methanol to form a suspension, stirred at 30° C. for 4 hrs, filtered, dried at room temperature for 1 hr and obtained 48 mg fumarate cocrystal form, yield 83%.

Example 18

Took 50 mg of LY2157299 monohydrate and mixed with 18.3 mg fumaric acid, added 1 mL of methanol to form a suspension, stirred at 10° C. for 16 hrs, filtered, dried at room temperature for 1 hr and obtained 51 mg fumarate cocrystal form, yield 89%.

Example 19

Took 30 mg of LY2157299 monohydrate and mixed with 11 mg fumaric acid, added 0.4 mL of isopropanol to form a suspension, stirred at 20° C. for 8 hrs, filtered, dried at room temperature for 1 hr and obtained 27 mg succinate cocrystal form, yield 78%.

Example 20

Took 20 mg of LY2157299 monohydrate and mixed with 6.1 mg fumaric acid, added 0.4 mL of n-butanol to form a suspension, stirred at 40° C. for 10 hrs, filtered, dried at room temperature for 1 hr and obtained 16 mg fumarate cocrystal form, yield 69%.

Example 21

Took 50 mg of LY2157299 monohydrate and mixed with 12.2 mg fumaric acid, added 0.5 mL of ethyl acetate to form a suspension, stirred at 40° C. for 4 hrs, filtered, dried at room temperature for 1 hr and obtained 38 mg fumarate cocrystal form, yield 66%.

Example 22

Took 50 mg of LY2157299 monohydrate and mixed with 10.7 mg fumaric acid, added 0.63 mL of acetone to form a suspension, stirred at 40° C. for 4 hrs, filtered, dried at room temperature for 1 hr and obtained 39 mg fumarate cocrystal form, yield 68%.

XRPD patterns, DSC plots, TGA plots (not shown) of the samples prepared in Examples 14 to 22 are the same as or similar to that of the sample prepared in Example 12, indicating the cocrystals obtained in Examples 14 to 22 are the same as that of Example 12.

Example 23

| Component (active ingredient basis) | Amount (mg) |
|---|---|
| LY2157299 succinate cocrystal form or LY2157299 fumarate cocrystal form | 80 |
| Microcrystalline cellulose | 310 |
| silicon dioxide | 5 |
| Talc | 5 |
| Total | 400 |

Mixed LY2157299 succinate cocrystal form or LY2157299 fumarate cocrystal form, starch, microcrystalline cellulose, silicon dioxide, and talc and then filled to capsules.

Example 24

| Component(active ingredient basis) | Amount(mg) |
|---|---|
| LY2157299 succinate cocrystal form or LY2157299 fumarate cocrystal form | 150 |
| Microcrystalline cellulose | 50 |
| Starch | 59 |
| Hydroxypropyl methylcellulose (5% water solution) | 5.0 |
| Carboxymethyl starch sodium | 4.5 |
| Magnesium stearate | 1.0 |
| Talc | 1.5 |
| Total | 270 |

Sieved LY2157299 succinate cocrystal form or LY2157299 fumarate cocrystal form, starch, and microcrystalline cellulose to a #20 sieve, and thoroughly mixed them. Mixed hydroxypropyl methylcellulose solution with the mixed powders, then pass it to a #16 sieve, dried the granules then passed a #16 sieve. Passed carboxymethyl starch sodium, magnesium stearate and talc to a #30 sieve, added them to the above granules, mixed and pressed into tablets using tablet press, each tablet weighed 150 mg.

Comparative Example 1

Performed apparent water solubility test on LY2157299 monohydrate of Preparation Example 1 and the LY2157299 succinate cocrystal form of Example 1, and the LY2157299 fumarate cocrystal form of example 12, the details are below:

Accurately weighed 5 mg samples in a 200 mL flask which was in a water bath with temperature 25° C.±2° C., added water in a geometric fashion the flask, stirred (about 200 r/min), and observed by naked eyes to see if it was clear. Water was added every 3 mins, maximum water amount 100 mL.

The results are shown in the following table. It shows the LY2157299 succinate cocrystal form and the LY2157299 fumarate cocrystal form both had better water solubility than the known LY2157299 monohydrate.

| Form | Solubility (μg/mL) |
|---|---|
| LY2157299 Monohydrate | <50 |
| LY2157299 succinate cocrystal form | 130 |
| LY2157299 fumarate cocrystal form | 330 |

The described above are only specific embodiments for illustrating the present invention, but without limiting it to that. Any changes or alternations, without creative work, made by those skilled in the art within the technical scope disclosed by the present invention, should fall within the scope of the present invention. Therefore, the scope of protection of the present invention shall be subject to the scope of protection defined in the claims.

What is claimed is:

1. A cocrystal of 2-(6-methyl-pyridin-2-yl)-3-(6-amido-quinolin-4-yl)-5,6-dihydro-4H-pyrrolo[1,2-b]pyrazole and succinic acid, wherein 2-(6-methyl-pyridin-2-yl)-3-(6-amido-quinolin-4-yl)-5,6-dihydro-4H-pyrrolo[1,2-b]pyrazole and succinic acid have a molar ratio of 1:0.5 and wherein the X-ray powder diffraction pattern of the cocrystal, using Cu-Kα radiation, expressed as 2θ angles, has the following characteristic peaks: 10.8°±0.2°, 11.6°±0.2°, 12.3°±0.2°, 15.5°±0.2°, 20.2°±0.2°, and 21.3°±0.2°.

2. The cocrystal according to claim 1, wherein the X-ray powder diffraction pattern of the cocrystal, using Cu-Kα radiation, expressed as 2θ angles, has one or more characteristic peaks in the following position: 16.8°±0.2°, 18.0°±0.2°, 21.7°±0.2°, 22.0°±0.2°, 24.6°±0.2° and 25.2°±0.2°.

3. The cocrystal according to claim 1 wherein the Fourier-transform infrared spectrum of the cocrystal, has the following characteristic peaks: 3473 cm$^{-1}$±2 cm$^{-1}$, 3141 cm$^{-1}$±2 cm$^{-1}$, 1693 cm$^{-1}$±2 cm$^{-1}$, 1580 cm$^{-1}$±2 cm$^{-1}$, 1429 cm$^{-1}$±2 cm$^{-1}$, 1322 cm$^{-1}$±2 cm$^{-1}$, 1189 cm$^{-1}$±2 cm$^{-1}$, 864 cm$^{-1}$±2 cm$^{-1}$, 831 cm$^{-1}$±2 cm$^{-1}$, 806 cm$^{-1}$±2 cm$^{-1}$ and 609 cm$^{-1}$±2 cm$^{-1}$.

4. A single-crystal of the cocrystal according to claim 1, wherein the single-crystal of the cocrystal belongs to the triclinic system, P1 space group and has the following single-crystal lattice parameters: a=7.8 Å±0.2 Å; b=11.5 Å±0.2 Å; c=12.6 Å±0.2 Å; α=87.3°±0.2°; β=78.1°±0.2°; γ=89.2°±0.2°.

5. A method of preparing the cocrystal according to claim 1, wherein the method comprises any one of the following methods:
  (1) adding a solvent to a mixture of 2-(6-methyl-pyridin-2-yl)-3-(6-amido-quinolin-4-yl)-5,6-dihydro-4H-pyrrolo[1,2-b]pyrazole (LY2157299) monohydrate and succinic acid, grinding to dryness to obtain the cocrystal; wherein
  the solvent is selected from the group consisting of methanol, acetonitrile, and water;
  the LY2157299 monohydrate and succinic acid has a molar ratio of 1:0.5 to 1:1.2,
  the weight to volume ratio of LY2157299 monohydrate to the solvent is from 80 mg:1 mL to 200 mg:1 mL, and
  the grinding temperature is 10 to 40° C.; or
  (2) forming a suspension of a mixture of LY2157299 monohydrate and succinic acid in a solvent, stirring for crystallization, separating crystals and drying to obtain the cocrystal;
  wherein:
  the solvent is selected from the group consisting of a C1 to C4 alcohol, ethyl acetate, and acetone;
  the LY2157299 monohydrate and succinic acid has a molar ratio of 1:0.5 to 1:1.2;
  the weight to volume ratio of LY2157299 monohydrate to the solvent is from 50 mg/mL to 100 mg/mL;
  the stirring temperature is from 10 to 40° C.; and
  the stirring time is 4 to 16 hours.

6. A cocrystal of 2-(6-methyl-pyridin-2-yl)-3-(6-amido-quinolin-4-yl)-5,6-dihydro-4H-pyrrolo[1,2-b]pyrazole and fumaric acid, wherein 2-(6-methyl-pyridin-2-yl)-3-(6-amido-quinolin-4-yl)-5,6-dihydro-4H-pyrrolo[1,2-b]pyrazole and fumaric acid have a molar ratio of 1:0.5 and wherein the X-ray powder diffraction pattern of the cocrystal, using Cu-Kα radiation, expressed as 2θ angles, has the following characteristic peaks: 8.3°±0.2°, 9.8°±0.2°, 15.5°±0.2°, 16.4°±0.2°, 16.7°±0.2°, and 23.7°±0.2°.

7. The cocrystal according to claim 6, wherein the X-ray powder diffraction pattern of the cocrystal form, expressed as 2θ angles, has one or more characteristic peaks in the following position: 23.4°±0.2°, 24.2°±0.2°, 27.1°±0.2°, and 28.3°±0.2°.

8. The cocrystal according to claim 6, wherein the Fourier-transform infrared spectrum of the cocrystal, has the following characteristic peaks: 3350 cm$^{-1}$±2 cm$^{-1}$, 3153 cm$^{-1}$±2 cm$^{-1}$, 1681 cm$^{-1}$±2 cm$^{-1}$, 1588 cm$^{-1}$±2 cm$^{-1}$, 1395 cm$^{-1}$±2 cm$^{-1}$, 1320 cm$^{-1}$±2 cm$^{-1}$, 1149 cm$^{-1}$±2 cm$^{-1}$, 971 cm$^{-1}$±2 cm$^{-1}$, 870 cm$^{-1}$±2 cm$^{-1}$, 835 cm$^{-1}$±2 cm$^{-1}$, 747 cm$^{-1}$±2 cm$^{-1}$ and 634 cm$^{-1}$±2 cm$^{-1}$.

9. A single-crystal of the cocrystal according to claim 6, wherein the single-crystal of the cocrystal belongs to triclinic system, P1 space group and has the following single-crystal lattice parameters: a=8.6 Å±0.2 Å; b=11.7 Å±0.2 Å; c=12.2 Å±0.2 Å; α=99.9°±0.2°; β=102.3°±0.2°; γ=108.4°±0.2°.

10. A method of preparing the cocrystal according to claim 6, wherein the method comprises any one of the following methods:

(1) adding a solvent to a mixture of 2-(6-methyl-pyridin-2-yl)-3-(6-amido-quinolin-4-yl)-5,6-dihydro-4H-pyrrolo[1,2-b]pyrazole (LY2157299) monohydrate and fumaric acid, grinding to dryness to obtain the cocrystal; wherein:

the solvent is selected from the group consisting of methanol, acetonitrile, and water;

the weight to volume ratio of the mixture to solvent is from 60 mg:1 mL to 160 mg:1 mL;

the LY2157299 monohydrate and fumaric acid has a molar ratio of 1:0.5 to 1:1.2; and the grinding temperature is 10 to 40° C.; or (2) forming a suspension of a mixture of LY2157299 monohydrate and fumaric acid in a solvent, stirring for crystallization, separating crystals and drying to obtain the cocrystal;

wherein:

the solvent is selected from the group consisting of a C1 to C4 alcohol, ethyl acetate, and acetone;

the LY2157299 monohydrate and fumaric acid has a molar ratio of 1:0.5 to 1:1.2;

the weight to volume ratio of LY2157299 monohydrate to the solvent is from 50 mg/mL to 100 mg/mL;

the stirring temperature is from 10 to 40° C.; and the stirring time is 4 to 16 hours.

11. A pharmaceutical composition comprising a therapeutically effective amount of the cocrystal according to claim 1 and at least one pharmaceutically acceptable carrier or additive.

12. The pharmaceutical composition according to claim 11, wherein the pharmaceutical composition is in a dosage form selected from the group consisting of tablet, powder, capsule, lozenge, emulsion, cream, syrup, sublingual, small medicine bag, flat capsule, elixirs gel, suspension, injectable, aerosol, ointment, suppository, and any combination thereof.

13. A pharmaceutical composition comprising a therapeutically effective amount of the cocrystal according to claim 6 and at least one pharmaceutically acceptable carrier or additive.

14. The pharmaceutical composition according to claim 13, wherein the pharmaceutical composition is in a dosage form selected from the group consisting of tablet, powder, capsule, lozenge, emulsion, cream, syrup, sublingual, small medicine bag, flat capsule, elixirs gel, suspension, injectable, aerosol, ointment, suppository, and any combination thereof.

* * * * *